United States Patent
Priegnitz et al.

(10) Patent No.: US 7,820,869 B2
(45) Date of Patent: Oct. 26, 2010

(54) BINDERLESS ADSORBENTS AND THEIR USE IN THE ADSORPTIVE SEPARATION OF PARA-XYLENE

(75) Inventors: James W. Priegnitz, Boulder Junction, WI (US); Darryl M. Johnson, Sr., Broadview, IL (US); Linda Shi Cheng, Highland Park, IL (US); Scott E. Commissaris, Fox River Grove, IL (US); Jack E. Hurst, Mobile, AL (US); Michael H. Quick, Arlington Heights, IL (US); Santi Kulprathipanja, Inverness, IL (US)

(73) Assignee: UOP LLC, Des Plaines, IL (US)

( * ) Notice: Subject to any disclaimer, the term of this patent is extended or adjusted under 35 U.S.C. 154(b) by 106 days.

(21) Appl. No.: 12/165,390

(22) Filed: Jun. 30, 2008

(65) Prior Publication Data

US 2009/0326309 A1    Dec. 31, 2009

(51) Int. Cl.
    C07C 7/12    (2006.01)
(52) U.S. Cl. .................. 585/827; 585/820; 585/828
(58) Field of Classification Search ............... 585/820, 585/828
    See application file for complete search history.

(56) References Cited

U.S. PATENT DOCUMENTS

| | | | |
|---|---|---|---|
| 3,119,659 A | 1/1964 | Taggert et al. | |
| 3,119,660 A | 1/1964 | Howell et al. | |
| 3,394,989 A | 7/1968 | Drost | |
| 3,433,587 A | 3/1969 | Haden et al. | |
| 3,997,620 A * | 12/1976 | Neuzil | 585/828 |
| 4,058,586 A | 11/1977 | Chi et al. | |
| 4,381,255 A | 4/1983 | Nozemack et al. | |
| 4,381,256 A | 4/1983 | Hildebrandt | |
| 4,424,144 A | 1/1984 | Pryor et al. | |
| 4,603,040 A | 7/1986 | Kuznicki et al. | |
| 4,818,508 A | 4/1989 | Flank et al. | |
| 4,853,355 A | 8/1989 | Behan et al. | |
| 5,026,531 A | 6/1991 | Tannous et al. | |
| 5,045,295 A | 9/1991 | Tannous et al. | |
| 5,107,062 A * | 4/1992 | Zinnen | 585/828 |
| 5,403,800 A | 4/1995 | Beck et al. | |
| 5,495,059 A | 2/1996 | Beck et al. | |
| 5,633,417 A | 5/1997 | Beck et al. | |
| 5,849,981 A * | 12/1998 | Kulprathipanja | 585/828 |
| 6,478,854 B1 | 11/2002 | Kotagiri et al. | |
| 6,537,348 B1 | 3/2003 | Hirano et al. | |
| 6,569,400 B1 | 5/2003 | Sterte et al. | |
| 6,576,582 B1 | 6/2003 | Beck et al. | |
| 6,699,811 B1 | 3/2004 | Mohr et al. | |
| 6,746,660 B1 | 6/2004 | Chiag et al. | |
| 6,777,583 B2 | 8/2004 | Beck et al. | |
| 6,858,129 B2 | 2/2005 | Mohr et al. | |
| 6,884,918 B1 * | 4/2005 | Plee et al. | 585/828 |
| 6,908,604 B2 | 6/2005 | Sterte et al. | |
| 6,919,491 B1 | 7/2005 | Cheng et al. | |
| 6,949,239 B2 | 9/2005 | Sterte et al. | |
| 7,008,896 B2 | 3/2006 | Stamires et al. | |
| 7,094,390 B2 | 8/2006 | Sterte et al. | |
| 7,267,812 B2 | 9/2007 | Takahashi et al. | |
| 2005/0197517 A1 | 9/2005 | Cheng et al. | |
| 2005/0266984 A1 | 12/2005 | Sterte et al. | |
| 2007/0032690 A1 | 2/2007 | Ghosh et al. | |
| 2008/0138619 A1 | 6/2008 | Miller | |

FOREIGN PATENT DOCUMENTS

| | | |
|---|---|---|
| CN | 1034276 C | 3/1997 |
| EP | 0 425 740 A1 | 10/1989 |
| EP | 1 679 286 A1 | 7/2006 |
| JP | 3146414 A2 | 6/1991 |
| JP | 4198011 A2 | 7/1992 |
| JP | 6183727 A2 | 7/1994 |
| JP | 2782744 B2 | 8/1998 |
| JP | 2000042418 A2 | 2/2000 |
| RU | 2124396 C1 | 1/1999 |

OTHER PUBLICATIONS

Kulprathipanja, S., "Adsorbent and Process for the Separation of Meta-Xylene from Aromatic Hydrocarbons," pending U.S. Appl. No. 12/165,266.

Kulprathipanja, S., "Binderless Adsorbents Comprising Nano-Size Zeolite X and Their Use in the Adsorptive Separation of Para-Xylene," pending U.S. Appl. No. 12/165,329.

Cheng, Linda Shi, "Binderless Adsorbents with Improved Mass Transfer Properties and Their Use in the Adsorptive Separation of Para-Xylene," pending U.S. Appl. No. 12/165,359.

Cheng, Linda Shi, "Adsorbents with Improved Mass Transfer Properties and Their Use in the Adsorptive Separation of Para-Xylene," pending U.S. Appl. No. 12/165,412.

U.S. Appl. No. 12/165,359, filed Jun. 30, 2008, Cheng et al.
U.S. Appl. No. 12/165,412, filed Jun. 30, 2008, Cheng et al.
U.S. Appl. No. 12/165,329, filed Jun. 30, 2008, Kulprathipanja et al.
U.S. Appl. No. 12/165,266, filed Jun. 30, 2008, Kulprathipanja et al.
International Search Report and Written Opinion dated Mar. 11, 2010, International Application No. PCT/US2009/047359, International filing date Jun. 15, 2009.

(Continued)

*Primary Examiner*—Tam M Nguyen
(74) *Attorney, Agent, or Firm*—David J Piasecki

(57) ABSTRACT

Adsorbents and methods for the adsorptive separation of para-xylene from a mixture containing at least one other $C_8$ aromatic hydrocarbon (e.g., a mixture of ortho-xylene, meta-xylene, para-xylene, and ethylbenzene) are described. Suitable binderless adsorbents (e.g., formulated with the substantial absence of an amorphous material that normally reduces selective pore volume), particularly those with a water content from about 3% to about 5.5% by weight, improve capacity and/or mass transfer. These properties are especially advantageous for improving productivity in low temperature, low cycle time adsorptive separation operations in a simulated moving bed mode.

19 Claims, 5 Drawing Sheets

OTHER PUBLICATIONS

International Search Report and Written Opinion dated Mar. 25, 2010, International Application No. PCT/US2009/046055, International filing date Jun. 3, 2009.

USPTO Office Action dated Mar. 9, 2010, U.S. Appl. No. 12/165,329, filed Jun. 30, 2008.

Response to Office Action dated Jun. 7, 2010 in U.S. Appl. No. 12/165,329, filed Jun. 30, 2008.

USPTO Office Action dated Mar. 9, 2010, U.S. Appl. No. 12/165,359, filed Sep. 22, 2008.

Response to Office Action dated Jun. 7, 2010, U.S. Appl. No. 12/165,359, filed Sep. 22, 2008.

USPTO Office Action dated Mar. 9, 2010 in U.S. Appl. No. 12/165,412, filed Jun. 30, 2008.

Response to Office Action dated Jun. 7, 2010, U.S. Appl. No. 12/165,412, filed Jun. 30, 2008.

* cited by examiner

US 7,820,869 B2

BINDERLESS ADSORBENTS AND THEIR USE IN THE ADSORPTIVE SEPARATION OF PARA-XYLENE

FIELD OF THE INVENTION

The present invention relates to adsorbents and methods for the adsorptive separation of para-xylene from a mixture containing at least one other $C_8$ alkylaromatic hydrocarbon (e.g., a mixture of ortho-xylene, meta-xylene, para-xylene, and ethylbenzene). In particular, binderless adsorbents, and particularly those with a water content from about 3% to about 5.5% by weight, have improved capacity and/or mass transfer properties, which benefit the adsorptive separation process.

DESCRIPTION OF RELATED ART $C_8$ alkylaromatic hydrocarbons are generally considered to be valuable products, with a high demand for para-xylene. In particular, the oxidation of para-xylene is used to commercially synthesize terephthalic acid, a raw material in the manufacture of polyester fabrics. Major sources of para-xylene include mixed xylene streams that result from the refining of crude oil. Examples of such streams are those resulting from commercial xylene isomerization processes or from the separation of $C_8$ alkylaromatic hydrocarbon fractions derived from a catalytic reformate by liquid-liquid extraction and fractional distillation. The para-xylene may be separated from a para-xylene-containing feed stream, usually containing a mixture of all three xylene isomers, by crystallization and/or adsorptive separation. The latter technique has captured the great majority of the market share of newly constructed plants for the production of para-xylene.

Accordingly, numerous patents are directed to the adsorptive separation of para-xylene from feed streams containing a mixture of $C_8$ alkylaromatics. Zeolites X and Y have been used to selectively adsorb para-xylene. See, for example, U.S. Pat. Nos. 3,686,342, 3,903,187, 4,313,015, 4,899,017, 5,171,922, 5,177,295, 5,495,061, and 5,948,950. U.S. Pat. No. 4,940,830 describes a rejective separation of para-xylene from other xylene isomers and ethylbenzene using sodium zeolite Y or a sodium zeolite Y that is also ion-exchanged with a Groups IB or Group VII element. A gas-phase process using adsorptive separation to recover para-xylene from a mixture of xylenes, with an adsorbent comprising a crystalline molecular sieve having an average crystal size between 0.5 and 20 microns is described in WO 2008/033200.

There remains a need in the art for improved adsorbents and processes for the efficient separation of para-xylene from a relatively impure mixture of $C_8$ alkylaromatic hydrocarbons.

SUMMARY OF THE INVENTION

The invention relates to adsorbents that selectively adsorb para-xylene over at least one other $C_8$ alkylaromatic compound present in a mixture. Due to the practical limitations of reaction equilibrium/selectivity, as well as evaporative (distillation) separations, typical mixtures obtained from oil refining processes contain the other xylene isomers, ortho-xylene and meta-xylene (in addition to para-xylene), in varying amounts and usually also contain ethylbenzene. Such mixtures will normally constitute feed streams used in methods associated with the invention.

Accordingly, embodiments of the invention are directed to processes for separating para-xylene from a relatively impure mixture of one or more $C_8$ alkylaromatic hydrocarbons other than the desired para-xylene. The mixture is contacted under adsorption conditions with an adsorbent comprising zeolite X. Aspects of the invention are related to the use of binderless adsorbents having a water content from about 3% to about 5.5%, which can provide highly favorable performance characteristics in the adsorptive separation of para-xylene. In particular, adsorptive para-xylene selectivity and adsorbent capacity are increased. Additionally, according to some embodiments, the mass transfer rate of (i) para-xylene into the zeolite pores during adsorption and (ii) desorbent into the zeolite pores to displace adsorbed para-xylene during desorption, are significantly greater, relative to conventional adsorbents comprising zeolite X and a non-selective (e.g., amorphous) binder. The mass transfer rate may be improved by modifying the crystallite size of the zeolite X, as discussed in greater detail below.

Therefore, binderless adsorbents as described herein are prepared from or comprise zeolite X. The zeolite X may have a conventional crystallite size (e.g., greater than 1.8 microns), but it is recognized that mass transfer may be improved if optionally at least a portion the zeolite X is characterized as "small-crystallite-size" (i.e., zeolite X having an average crystallite size below 1.8 microns, and typically from about 500 nanometers to about 1.5 microns) and/or even "nano-size zeolite X" (i.e., zeolite X having an average crystallite size below 500 nanometers, and typically from about 20 nanometers to about 300 nanometers). Portions of zeolite X, and particularly a "prepared" (or already made) portion having a particular average crystallite size as discussed above (e.g., small-crystallite-size) is present in the adsorbent in an amount of at least 60% by weight, and often from about 70% to about 90% by weight. The balance of the adsorbent may comprise a "converted" portion, resulting from the conversion of a zeolite X-precursor to zeolite X. The converted portion of zeolite X, like the prepared portion, may have a conventional crystallite size, or may be either small-crystallite-size or nano-size zeolite X, as described above.

The increases in capacity and/or mass transfer rate of binderless adsorbents comprising zeolite X, and particularly those having a water content as described above, are especially advantageous in the case of low temperature operation (e.g., less than about 175° C. (350° F.)), where mass transfer and/or capacity limitations associated with conventional, bound zeolite X-containing adsorbents, having a significant amount of non-selective pore volume, are more commercially significant. Low temperature operation is desirable for a number of reasons, including even greater para-xylene adsorptive selectivity and adsorbent capacity, as well as increased liquid feed density, all of which directionally improve para-xylene productivity. Yet in a simulated moving bed mode of operation, which is often used in continuous industrial processes for the adsorptive separation of para-xylene from a feed mixture of ortho-xylene, meta-xylene, para-xylene, and ethylbenzene, these advantages associated with lower operating temperatures have been found to diminish as cycle time decreases, due to mass transfer limitations affecting the rate of para-xylene adsorption/desorption. Adsorbents having improved mass transfer properties (e.g., as a result of reduction of the zeolite X average crystallite size as discussed below) can therefore exploit the improvements in para-xylene capacity and selectivity, as discussed above, associated with lower temperature operation. Increased para-xylene productivity and consequently improved process economics, are made possible.

In formulating a "binderless" adsorbent comprising zeolite X, a zeolite X-precursor such as a clay (e.g., kaolin clay), is mixed with a prepared (or already made) portion of zeolite X and the precursor is then itself substantially converted to zeolite X. Like the prepared portion, the converted portion of zeolite X may have a conventional average crystallite size (e.g., greater than 1.8 microns), or optionally may be small-crystallite-size zeolite X or nano-size zeolite X, having the associated average crystallite sizes discussed above. In any event, the elimination or substantial elimination of a conventional binder, which normally contributes only non-selective pore volume, can significantly increase adsorbent capacity for (i) a desired extract component (e.g., para-xylene) and/or (ii) a desorbent (e.g., para-diethylbenzene).

Binderless adsorbents having a water content in the ranges described herein additionally have comparable or improved adsorption selectivity for the desired product para-xylene. Thus, both the para-xylene/meta-xylene and para-xylene/ortho-xylene adsorption selectivities are similar or increased, relative to conventional, bound adsorbents. Para-xylene/ethylbenzene selectivity is increased, while desorbent strength is maintained. These selectivity, capacity, and/or mass transfer advantages can translate to a 15-35% improvement in para-xylene productivity associated with the binderless adsorbents described herein, when compared to conventional, bound adsorbents having a water content of 4-6% by weight but otherwise operating under identical processing conditions (i.e., maintaining all other operating parameters, such as feed composition and process variables, constant). Furthermore, attrition and strength properties of the binderless adsorbents, as measured by water attrition and piece crush strength analyses, show additional, physical property improvements over conventional adsorbents.

In addition to kaolin clay, another zeolite X-precursor is meta-kaolin clay, which results from the activation of kaolin clay at elevated temperature. Whether kaolin or meta-kaolin is used as the starting, zeolite X-precursor, the conversion of this zeolite X-precursor, which may initially be used to bind a first portion of zeolite X, may generate a second (e.g., converted) portion of zeolite X, having a silica to alumina molar ratio that differs from that of the first (e.g., already made or prepared) portion.

Other aspects of the invention, however, are directed to the use of a silica source, during conversion of the zeolite X-precursor, to increase the silica to alumina molar ratio of the second portion of zeolite X, to a value above that of the zeolite X-precursor, and often comparable to that of the first portion of zeolite X. Thus, after conversion, a resulting, exemplary adsorbent may comprise first and second portions of zeolite X, both having a $SiO_2/Al_2O_3$ molar ratio from about 2.3 to about 2.7. As discussed above, the first and second portions may have different average crystallite sizes. For example, the first portion may be small-crystallite-size zeolite X having an average crystallite size from about 500 nanometers to about 1.5 microns, while the second portion may be zeolite X having a conventional crystallite size of greater than 1.8 microns.

Other aspects of the invention therefore relate to a method of preparing a binderless adsorbent having improved capacity and/or mass transfer properties. The method comprises forming particles comprising zeolite X and a zeolite X-precursor (e.g., kaolin clay), activating the zeolite X-precursor of the particles at a temperature from about 500° C. to about 700° C. (about 930° F. to about 1300° F.), and digesting the particles comprising activated zeolite X-precursor with a caustic solution to obtain the binderless adsorbent. The caustic digestion step may be performed in the presence of a silica source (e.g., sodium silicate or colloidal silica) to increase the silica to alumina molar ratio of the converted portion of zeolite X in the adsorbent, above that of the zeolite X-precursor. The use of a silica source, and the corresponding increase in the silica to alumina molar ratio of the converted zeolite X, can result in additional advantages, such as increased desorbent strength, which benefit the overall process performance in the adsorptive separation of para-xylene.

The zeolite X used to formulate binderless adsorbents for adsorptive separations will generally have a molecular silica to alumina ($SiO_2/Al_2O_3$) molar ratio from about 2.0 to about 4.0, corresponding to an atomic Si/Al ratio from about 1.0 to about 2.0. These ratios generally apply not only to a first or "prepared" portion of zeolite X that is originally bound with a zeolite X-precursor such as meta-kaolinite, but also to the "converted" zeolite X resulting from the conversion of the zeolite X-precursor. However, as indicated above, the binderless zeolite X may have portions with somewhat different silica to alumina molar ratios as a result of different types of zeolite X in these portions (i.e., prepared and/or converted) of the final adsorbent, as well as the addition of a silica source during the conversion of the zeolite X-precursor to increase the silica to alumina molar ratio of the converted portion.

The zeolite, regardless of whether a prepared or converted portion, normally has at least 95%, and typically substantially all (at least 99%), of its ion-exchangeable sites exchanged with barium or a combination of barium and potassium. A representative adsorbent comprises zeolite X having from about 60% to about 100% of its ion-exchangeable sites exchanged with barium and from about 0% to about 40% of its ion-exchangeable sites exchanged with potassium.

The binderless adsorbents comprising zeolite X, and optionally having a water content as discussed above, may be used in solid adsorbents employed in fixed bed, moving bed, or simulated moving bed adsorptive separation processes employing conventional adsorption conditions. Adsorption may be performed in the liquid or gas phase, with liquid phase adsorption conditions normally being favored. When employed for the adsorptive separation of para-xylene in a simulated moving bed mode, the high adsorbent capacity/mass transfer properties of the adsorbents described above allow for relatively increased para-xylene productivity, especially in the case of low cycle time operation, in comparison to conventional adsorbents operating at the same overall percentage of para-xylene recovery. That is, the adsorbent bed concentration profiles are not adversely affected when cycle time is, for example, less than about 34 minutes (e.g., in the range from about 24 minutes to about 34 minutes). The cycle time of a simulated moving bed adsorptive separation process refers to the time for any of the inlet or outlet streams to return to its original adsorbent bed position. Therefore, in a typical simulated moving bed mode of operation with 24 adsorbent beds (e.g., two vessels each having 12 beds), the cycle time refers, for example, to the time required for the inlet feed stream, initially introduced into the first bed at time zero, to again be introduced to this bed. All other factors (e.g., para-xylene purity and recovery) being equal, shorter cycle times translate to higher productivity.

Particular embodiments of the invention thus relate to a process for separating para-xylene from a mixture comprising at least one other $C_8$ alkylaromatic hydrocarbon, with the mixture normally containing the xylene isomers ortho- and meta-xylene as well as ethylbenzene. The process comprises contacting the mixture with a binderless adsorbent comprising zeolite X and having a water content from about 3% to about 5.5% by weight. The prepared and converted portions of zeolite X may independently have average zeolite crystallite sizes in the ranges discussed above as being characteristic of (i) conventional crystallite sizes, (ii) small-crystallite size zeolite X, or (iii) nano-size zeolite X. Exemplary adsorption temperatures range from about 60° C. (140° F.) to about 250° C. (480° F.). However, by virtue of their improved capacity and/or mass transfer properties, these adsorbents do not impose the appreciable limitations (e.g., mass transfer) associated with conventional adsorbents, in the case of low temperature operation. Therefore, as explained above, the benefits associated with improved adsorptive para-xylene selectivity and adsorbent capacity at relatively low temperatures can be more fully realized. Adsorption temperatures of less than about 175° C. (350° F.), for example from about 130° C. (270° F.) to about 165° C. (330° F.), are particularly advantageous when used with the adsorbents described above. Adsorption pressures may range from slightly above atmospheric pressure, for example about 1 barg (15 psig) to about 40 barg (580 psig).

The contact between the mixture of $C_8$ alkylaromatic hydrocarbons described above (e.g., as a continuous or batch process feed stream) and the binderless adsorbent effects or brings about the adsorption of para-xylene into the zeolite X pores, in preference to at least one other $C_8$ alkylaromatic hydrocarbon and normally in preference to all of such hydrocarbons present in the mixture. Therefore, an adsorbed phase (i.e., within the zeolite X pores) will be selectively enriched in para-xylene content, relative to that of the mixture of $C_8$ alkylaromatic compounds (e.g., the feed stream). If the mixture contains ortho-xylene, meta-xylene, para-xylene, and ethylbenzene, then para-xylene will be present in the adsorbed phase, in an enriched amount relative to the mixture, and ortho-xylene, meta-xylene, and ethylbenzene will be present in the non-adsorbed phase, in enriched amounts relative to the mixture.

The non-adsorbed phase may then be removed from (or flushed) from contact with the adsorbent, for example in a raffinate stream. The adsorbed phase, enriched in para-xylene, may be separately desorbed from the adsorbent, for example in an extract stream. A desorbent stream comprising a desorbent, for example an aromatic ring-containing compound such as toluene, benzene, indan, para-diethylbenzene, 1,4-diisopropylbenzene, or a mixture thereof may be used for both the flushing and desorption. An exemplary adsorptive separation process utilizing adsorbents discussed above may be performed in a simulated moving bed mode. According to this embodiment, a $C_8$ alkylaromatic hydrocarbon feed stream as described above and the desorbent stream are charged into a fixed bed of the adsorbent, while the extract and raffinate streams are removed from the bed. The charging and removal of these streams may be performed continuously.

During a simulated moving bed mode or other type of adsorptive separation mode, it may be desired to monitor the water content of an outlet stream, such as an extract or raffinate stream, in order to determine the water content or level of hydration of the adsorbent, and/or to maintain this water content in the range from about 3% to about 5.5% by weight, and preferably from about 3.5% to about 4.5% by weight. If necessary, water may be added to an inlet stream, such as a feed stream and/or desorbent stream, either continuously or intermittently, to maintain a desired level of adsorbent water level or hydration (e.g., corresponding to a target Loss in Ignition that is associated with the desired water content in the ranges discussed above). Alternatively, water may be added to obtain an absolute water content in the extract stream and/or raffinate stream, for example, from about 20 ppm by weight to about 120 ppm by weight, corresponding to the desired adsorbent water content in the above ranges.

These and other aspects and features relating to the present invention are apparent from the following Detailed Description.

DETAILED DESCRIPTION

Figure 1:
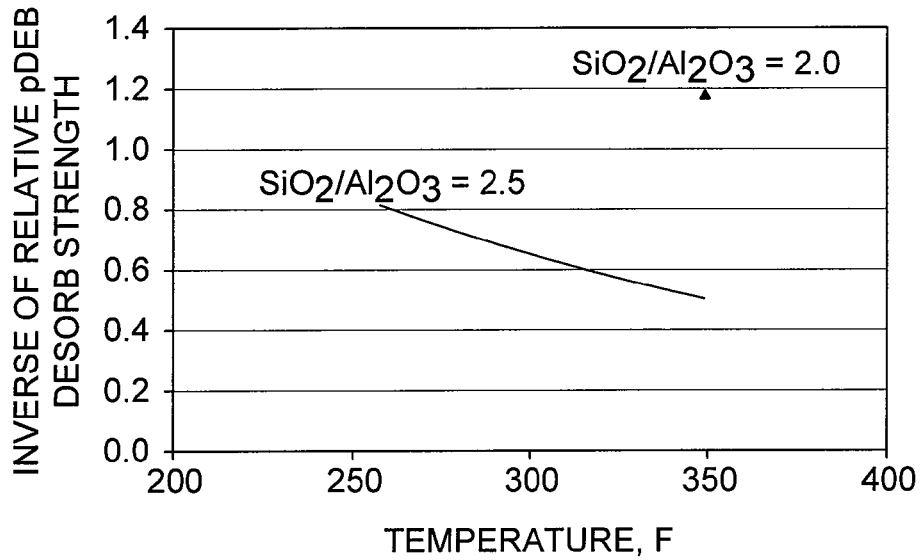
FIG. 1 shows the impact of reducing the barium-exchanged zeolite X silica to alumina molar ratio, from 2.5 to 2.0, on the strength of the para-diethylbenzene desorbent.

The invention relates to the separation of para-xylene from a mixture comprising at least one other $C_8$ alkylaromatic hydrocarbon. The term separation refers to the recovery of para-xylene in a stream (e.g., a product stream) or fraction having an enriched para-xylene content (i.e., a content that is higher than initially present in the mixture). The separation is achieved through contacting the mixture with a binderless adsorbent comprising zeolite X. The adsorbent can have a water content from about 3.5% to about 5.5% by weight, and preferably from about 3.5% to about 4.5% by weight. As discussed above, the use of a binderless adsorbent and/or operation at a relatively low water content directionally improves the selective micropore capacity for para-xylene and other $C_8$ alkylaromatics and thereby allows for increased production rates for a given operation. In addition, the use of binderless adsorbents and particularly those having prepared and/or converted portions of small-crystallite-size zeolite X and/or nano-size zeolite X can overcome mass transfer limitations to fully exploit the advantages of thermodynamically favorable operating regimes (e.g., at low temperatures and low cycle times).

The structure of zeolite X is described in detail in U.S. Pat. No. 2,882,244. Small-crystallite-size zeolite X can be prepared from a seeded synthesis, where a seed or initiator material, used as a means of nucleation or starting zeolite crystallite growth, is first prepared and then blended into a gel composition at a gel composition:seed ratio corresponding to a targeted crystallite size. The ratio of gel composition to seed governs the relative number or concentration of nucleation sites, which in turn affects the crystallite size of the zeolite X that is synthesized. Higher amounts or concentrations of seed directionally reduce the crystallite size. For example, zeolite X preparations having average crystallite sizes of 2 microns and 0.5 microns can be made using gel:seed ratios of about 5400:1 and 85:1, by weight, respectively. In view of the present disclosure, those having skill in the art can readily vary the weight ratios to achieve other average crystallite sizes. A typical gel composition comprises $Na_2O$, $SiO_2$, $Al_2O_3$, and water. For each mole of $Al_2O_3$, about 1-5 moles of $Na_2O$ and $SiO_2$, and about 100-500 moles of water, can be used in the gel.

The gel composition may be prepared by combining a gel makeup solution with an aluminate makeup solution containing, for example, about 12% alumina by weight. The gel makeup solution is prepared by mixing water, caustic solution, and sodium silicate, and cooling the mixture to about 38° C. (100° F.). The aluminate makeup solution is prepared by dissolving alumina trihydrate in a caustic solution, with heating as necessary for dissolution, followed by cooling and aging at about 38° C. (100° F.) prior to combining it with the gel makeup solution. The gel makeup solution and aluminate solution are then combined under vigorous agitation for a short period (e.g., about 30 minutes), prior to adding the required amount of seed.

The seed is prepared in a similar manner to the gel composition. A typical seed composition therefore also comprises $Na_2O$, $SiO_2$, $Al_2O_3$, and water. For each mole of $Al_2O_3$, about 10-20 moles of $Na_2O$ and $SiO_2$, and about 150-500 moles of water, can be used. The aluminate solution used in preparing the seed may contain, for example, about 18% alumina by weight. After the gel composition and seed are combined, the mixture is heated while agitation is maintained, and then aged under agitated conditions for a time from about 5 to about 50 hours and at a temperature from about 25° C. (75° F.) to about 150° C. (300° F.) to achieve the desired crystallite formation from the seed nuclei. The resulting solid material may then by filtered, washed, and dried to obtain the prepared, small-crystallite-size zeolite X.

Nano-size zeolite X having an average crystallite size in the ranges described above may be prepared according to the procedures described in application publication US 2007/0224113, incorporated by reference herein in its entirety. Zeolite crystallites refer to individual crystals as opposed to agglomerated crystals which are usually referred to as zeolite particles. The average crystallite size may be determined from Scanning Electron Microscopy (SEM) analysis of zeolite X crystallites.

In general, the nano-size zeolites which can be synthesized include any of the zeolites having a composition represented by the empirical formula:

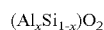

$(Al_xSi_{1-x})O_2$ where Al and Si are framework elements present as tetrahedral oxide units and "x" has a value from greater than 0 to about 0.5. Specific structure types of zeolites which can be prepared include zeolite X as well as a number of other zeolite structure types including, but not limited to, zeolite Y, structure types BEA, FAU, MFI, MEL, MTW, MOR, LTL, LTA, EMT, ERI, FER, MAZ, MEI, TON, and MWW.

One necessary part of the nano-size zeolite synthesis process is an initiator. The initiator is a concentrated, high pH aluminosilicate solution which can be clear or cloudy and has a composition represented by an empirical formula of:

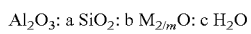

$Al_2O_3: a\ SiO_2: b\ M_{2/m}O: c\ H_2O$ where "a" has a value from about 4 to about 30, "b" has a value from about 4 to about 30, and "c" has a value from about 50 to about 500, "m" is the valence of M and has a value of +1 or +2 and M is a metal selected from the group consisting of alkali metals, alkaline earth metals and mixtures thereof with preferred metals being lithium, sodium, potassium and mixtures thereof. The initiator is obtained by mixing reactive sources of Al, Si and M plus water.

Accordingly, the aluminum sources include but are not limited to, aluminum alkoxides, precipitated alumina, aluminum hydroxide, aluminum salts and aluminum metal. Specific examples of aluminum alkoxides include, but are not limited to aluminum orthosec-butoxide, and aluminum orthoisopropoxide. Sources of silica include but are not limited to tetraethylorthosilicate, fumed silicas, precipitated silicas and colloidal silica. Sources of the M metals include but are not limited to the halide salts, nitrate salts, acetate salts, and hydroxides of the respective alkali or alkaline earth metals. When M is sodium, preferred sources are sodium aluminate and sodium silicate. The sodium aluminate is synthesized in situ by combining gibbsite with sodium hydroxide. Once the initiator is formed it is aged at a temperature of about 0° C. to about 100° C. for a time sufficient for the initiator to exhibit the Tyndall effect. Usually the time varies from about 1 hr to about 14 days and preferably from about 12 hours to about 10 days.

A second component of the nano-size zeolite synthesis process is a reaction solution from which the desired zeolite will be synthesized. This solution will have a composition represented by an empirical formula of:

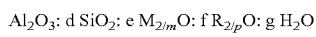

$Al_2O_3: d\ SiO_2: e\ M_{2/m}O: f\ R_{2/p}O: g\ H_2O$ where "d" has a value from about 4 to about 30, "e" has a value from about 4 to about 30, "f" has a value from 0 to about 30 and "g" has a value from about 5 to about 500, "p" is the valence of R and has a value of +1 or +2, R is an organoammonium cation selected from the group consisting of quaternary ammonium ions, protonated amines, protonated diamines, protonated alkanolamines, diquaternary ammonium ions, quaternized alkanolamines and mixtures thereof, the reaction solution formed by combining reactive sources of Al, Si, M and R plus water. The sources of aluminum, silicon and M are as described above, while the sources of R include but are not limited to hydroxide, chloride, bromide, iodide and fluoride compounds. Specific examples include without limitation ethyltrimethylammonium hydroxide (ETMAOH), diethyldimethylammonium hydroxide (DEDMAOH), propylethyldimethylammonium hydroxide (PEDMAOH), trimethylpropylammonium hydroxide, trimethylbutylammonium hydroxide (TMBAOH), tetraethylammonium hydroxide, hexamethonium bromide, tetramethylammonium chloride, N,N,N,N',N',N'-hexamethyl 1,4 butanediammonium hydroxide and methyltriethylammonium hydroxide. The source of R may also be neutral amines, diamines, and alkanolamines. Specific examples are triethanolamine, triethylamine, and N,N,N',N'tetramethyl-1,6-hexanediamine.

A reaction mixture is now formed by mixing the initiator and reaction solution. Usually the initiator is slowly added to the reaction solution and stirred for an additional period of time to ensure homogeneity. The resultant reaction mixture is now charged to an autoclave and reacted under autogenous pressure at a temperature of about 25° C. to about 200° C. for a time of about 1 hr to about 40 days. Reaction can be carried out either with or without stirring. After reaction is complete, the solid zeolite is separated from the reaction mixture by means well known in the art such as filtration or centrifugation, washed with deionized water and dried in air at ambient temperature up to about 100° C. The exchangeable cations M and R can be exchanged for other desired cations and in the case of R can be removed by heating to provide the hydrogen form of the nano-size zeolites.

Conventional zeolite X, small-crystallite-size zeolite X, or nano-size zeolite X may then be used in the synthesis of a binderless adsorbent by combining this "prepared" or already made portion with a zeolite X-precursor. Zeolite X-precursors include clays such as kaolin, kaolinites, and halloysite, and other minerals such as hydrotalcites, and solid silica and alumina sources such as precipitated and fumed amorphous silica, precipitated alumina, gibbsite, boemite, bayerite, and transition aluminas such gamma and eta alumina, and zeolite seed solutions and suspensions obtained from sodium silicate and sodium aluminate and similar reagents, which can be formed in an intimate mixture with the crystallites of a prepared portion of zeolite X. The forming procedure involves combining the zeolite X-precursor, exemplified by kaolin clay, with the zeolite X powder of the prepared portion of zeolite X and optionally other additives such as pore generating materials (e.g., corn starch to provide macroporosity) and water as needed to obtain the proper consistency for shaping. Shaping or forming into larger beads, spheres, pellets, etc., can be performed using conventional methods including bead forming processes such as Nauta mixing, tumbling, or drum rolling to prepare larger particles (e.g., in the range of about 16-60 Standard U.S. Mesh size). The formed particles comprising the prepared portion of zeolite X and the zeolite X-precursor are then activated at a temperature generally ranging from about 500° C. to about 700° C. (about 930° F. to about 1300° F.). In the case of a zeolite X-precursor comprising kaolin clay, activation causes this material to undergo endothermic dehydroxylation, whereby the disordered, meta-kaolin phase is formed.

Following activation, caustic digestion of the formed particles (e.g., using sodium hydroxide), then converts the activated zeolite X-precursor into zeolite X itself, resulting in a binderless adsorbent that may comprise or consist essentially of zeolite X having an average crystallite size associated with (i) conventional zeolite X, (ii) small-crystallite-size zeolite X, or (iii) nano-size zeolite X, as discussed above. Otherwise, the binderless adsorbent may comprise or consist essentially of a prepared portion of zeolite X having any of these average crystallite sizes associated with (i), (ii), or (iii) in combination with a converted portion of zeolite X having any other of these average crystallite sizes.

The silica to alumina molar ratio of the converted portion of zeolite X, as well as the contribution of this material in the final adsorbent formulation, may be varied according to the type and amount of zeolite X-precursor that is incorporated into the formed particles. Normally, the silica to alumina ratio of the zeolite X-precursor will be substantially conserved upon conversion into zeolite X. Thus, a typical kaolin clay having a $SiO_2/Al_2O_3$ molar ratio from about 2.0 to about 2.2 will convert to a zeolite X portion having a zeolite framework ratio within this range. It is possible, therefore, to prepare binderless adsorbents having first (prepared) and second (converted) portions of zeolite X with differing silica to alumina ratios.

However, aspects of the invention are associated with the finding that increasing the silica to alumina ratio of zeolite X, from a range of about 2.0 to about 2.2 to a range from about 2.1 to about 2.7, results in increased desorbent strength (e.g., with para-diethylbenzene desorbent) in the adsorptive separation of para-xylene. This is illustrated in FIG. 1, showing the impact of reducing the barium-exchanged zeolite X silica to alumina molar ratio, from 2.5 to 2.0, on the strength of the para-diethylbenzene desorbent. The line in FIG. 1 was generated from data using pulse and breakthrough (or dynamic) testing, as described in greater detail below, of an adsorbent comprising barium-exchanged zeolite X having a silica to alumina molar ratio of 2.5. In particular, the line shows the relationship between the inverse of the relative desorbent strength and adsorbent bed temperature.

When zeolite X having a silica to alumina molar ratio of 2.0 is substituted for higher ratio zeolite X in the adsorbent formulation, the para-diethylbenzene desorbent strength is reduced considerably (i.e., the value of the inverse of the relative desorbent strength increases), as shown in FIG. 1 by the data point (triangle) obtained for the lower ratio zeolite X. This reduction in desorbent strength, which affects the ability of the desorbent to displace the desired para-xylene product into an extract stream, can have adverse consequences in terms of obtaining para-xylene with a high purity and recovery, particularly in a commercial process for the adsorptive separation of para-xylene operating in a simulated moving bed mode.

These results illustrate the process efficiencies that can be gained from the use of binderless adsorbents in which the converted portion of zeolite X has a silica to alumina molar ratio in the range from about 2.1 to about 2.7, which may be the same or substantially the same as that for the prepared portion of zeolite X. However, zeolite X-precursors such as kaolin clay often have lower silica to alumina molar ratios, for example about 2.0, and therefore normally do not convert to the desired, higher ratio zeolite X.

However, aspects of the invention are associated with the finding that it is possible to modify the procedure in which the zeolite X-precursor is converted to zeolite X, in synthesis of a binderless adsorbent, to increase the silica to alumina molar ratio of the converted portion of zeolite X. In particular, it has been discovered that the procedure in which the zeolite X-precursor is converted to zeolite X, in synthesis of a binderless adsorbent, may be modified to increase the silica to alumina molar ratio of the converted portion of zeolite X. This may be achieved through the addition of silica source such as colloidal silica sol, silicic acid, sodium silicate, silica gel, or reactive particulate silica (e.g., diatomaceous earth, Hi-Sil, etc.). The silica source can be added during the adsorbent particle forming step, to the caustic digestion step, or both. The amount of silica added is such that the overall reaction mixture of zeolite X-precursor (e.g., meta-kaolin) and the silica source is controlled such that the reaction composition falls into the following range: $Na_2O/SiO_2=0.8-1.5$, $SiO_2/Al_2O_3=2.5-5$, $H_2O/Na_2O=25-60$.

The use of a separate source of silica can therefore allow the preparation of binderless adsorbents in which the silica to alumina molar ratio of both the prepared and converted portions of zeolite X are closely matched (e.g., are both within the range from about 2.0 to about 3.0, and normally from about 2.1 to about 2.7), thereby overcoming the drawbacks discussed above with respect to the use of lower ratio zeolite X in the adsorptive separation of para-xylene. Advantageously, the increase in the silica to alumina molar ratio of the converted portion of zeolite X can also improve the hydrothermal stability of the resulting binderless adsorbent.

The relative amounts of the prepared and converted portions of zeolite X in the binderless adsorbent may be varied. According to some embodiments, the amount of zeolite X-precursor used in the preparation of the formed particle will be in the range from about 5% to about 40% by weight, and usually from about 10% to about 30% by weight. These ranges therefore also correspond to the amounts of converted zeolite X that is present in representative binderless adsorbents described herein.

Various other embodiments associated with binderless adsorbents comprising zeolite X are possible. For example, if the zeolite X-precursor converts zeolite X having a desired average crystallite size, silica to alumina molar ratio, and other properties, then the binderless adsorbent may comprise predominantly or entirely, or consist essentially of, this converted zeolite X. To synthesize an adsorbent comprising all or substantially all converted zeolite X, the zeolite X-precursor may be shaped or formed into larger beads, spheres, pellets, etc., using conventional methods described above to prepare larger particles (e.g., in the range of about 16-60 Standard U.S. Mesh size), but without addition of a prepared portion of zeolite X.

According to some embodiments, a nano-size zeolite X (i.e., zeolite X having an average crystallite size below 500 nanometers, and typically from about 20 nanometers to about 300 nanometers) may be obtained as a converted portion from a zeolite X-precursor. Associated with the embodiments discussed above in which the converted portion of zeolite X is small-crystallite size or nano-size zeolite X, types of zeolite X-precursors that may be converted to zeolite X having these modified crystallite sizes include, but are not limited to, sodium silicate, sodium aluminate, aluminum sulfate, aluminum nitrate, aluminum chlorohydrate, and/or fumed, precipitated, colloidal, organometallic or other solid or liquid sources of silicon (or silica) or aluminum (or alumina). Such other sources include clays and related minerals, and those derived from a combination of two or more of the precursors described above to form aluminosilicate precursors, such as amorphous aluminosilicate co-precipitates, sol-gels or other solids formed therefrom. The zeolite X crystallite size is controlled in the ranges discussed above with respect to small-crystallite-size zeolite X or nano-size zeolite X by reaction pH, time, temperature, degree of agitation, and concentration of reagents, including those discussed and others, such as sodium hydroxide or other mineralizers. The zeolite X crystallite size of the converted portion can also be varied by varying the particle size of the zeolite X-precursor, such as kaolin or halloysite clay. A High Resolution Scanning Electron Microscopy (HR SEM) micrograph of a binderless adsorbent confirmed that the zeolite X-precursor converted to nano-size zeolite X.

Binderless adsorbents described herein may therefore comprise a prepared portion of zeolite X and a converted portion of zeolite X. The prepared and converted portions may be made according to the procedures described above, for example using the small-crystallite-size or nano-size zeolite X synthesis procedures above to make the prepared portion and using the conversion procedures above to make the converted portion. These adsorbents may then be employed in the adsorptive separation of para-xylene, according to procedures described herein. Those having skill in the art and consulting the present disclosure will appreciate that, with respect to the prepared and converted portions of zeolite X, the silica to alumina molar ratios, average crystallite sizes, relative amounts, and other properties, will depend on the desired characteristics of the resulting adsorbent, including strength, ion-exchange capacity, adsorbent capacity, desorbent selectivity, mass transfer, etc., for a given application.

In exemplary binderless adsorbents, non-zeolitic material is substantially absent (e.g., is present in the adsorbent generally in an amount of less than about 2% by weight, typically less than 1% by weight, and often less than 0.5% by weight). The absence or substantial absence of non-zeolitic or amorphous material may be confirmed by analysis of the binderless adsorbent using X-ray diffraction and/or high resolution scanning electron microscopy (HR-SEM) to verify crystal structure. Macro- and micro-pore structure and distribution may by characterized and confirmed using mercury porosimetry or liquid oxygen adsorption.

The portions of prepared zeolite X (e.g., small-crystallite-size zeolite X) and converted zeolite X in the binderless adsorbent may be in their sodium form initially, and the sodium cations may be partially or wholly exchanged by different cations, such as barium, potassium, strontium, and/or calcium, using known techniques. For example, the binderless adsorbent, synthesized with zeolite X having at least some of its ion-exchangeable sites in sodium ion form, may be immersed in a barium ion containing solution, or a barium and potassium ion containing solution, at conditions of time and temperature (e.g., about 0.5 to about 10 hours at about 20 to about 125° C.) which can effect ion exchange or replacement of sodium ions with barium and/or potassium ions. Ion-exchange can also be conducted in a column operation according to known techniques, for example by pumping preheated barium chloride/potassium chloride solutions through a column of the adsorbent particles to completely displace the sodium cations of the small-crystallite-size zeolite X. Filtration of the binderless adsorbent, removal from the solution, and re-immersion in a fresh solution (e.g., having the same or different ratios or cations or other types of cations) can be repeated until a desired level of exchange, with the desired types and ratios of cations, is achieved. Normally, the binderless adsorbents, comprising typically both prepared and converted portions of zeolite X, will have at least 95% or substantially all (e.g., at least 99%) of the zeolite X ion-exchangeable sites exchanged with barium or a combination of barium and potassium. Generally, no other metal ions occupy ion-exchangeable sites of the prepared portion of zeolite X (e.g., small-crystallite-size zeolite X) or the converted portion of zeolite X in an amount effective to alter the adsorptive properties of the adsorbent. In a representative embodiment, the zeolite X of the binderless adsorbent will have from about 60% to about 100% of its ion-exchangeable sites exchanged with barium and from about 0% to about 40% of its ion-exchangeable sites exchanged with potassium.

The number of ion-exchangeable sites decreases as the overall $SiO_2/Al_2O_3$ molar ratio of the zeolite X increases. The overall ratio may be affected by varying the ratio of either or both of the prepared zeolite X and converted zeolite X portions. Also, the total number of cations per unit cell decreases as monovalent cations (e.g., $K^-$) are replaced by divalent cations (e.g., $Ba^{+2}$). Within the zeolite X crystal structure, there exist many ion-exchangeable site locations, some of these being in positions outside of the supercages. Overall, the number and locations of cations in the zeolite crystal structure will depend upon the sizes and numbers of the cations present, as well as the $SiO_2/Al_2O_3$ molar ratio of the zeolite.

Those skilled in the art will recognize that the performance of an adsorbent (e.g., in terms of para-xylene purity and recovery into an extract stream) is influenced by a number of process variables, including operating conditions, feed stream composition, water content, and desorbent type and composition. The optimum adsorbent composition is therefore dependent upon a number of interrelated variables. In general, processes for the adsorptive separation of para-xylene from a mixture containing at least one other $C_8$ alkylaromatic hydrocarbon, as described herein, can achieve high para-xylene purity (e.g., at least about 99 wt-% or even at least about 99.5 wt-%) in the extract product stream with a high overall recovery of para-xylene from the feed stream (e.g., at least about 90%, from about 92% to about 99.5%, or from about 95% to about 99%).

One consideration associated with overall adsorbent performance is its water content, which may be approximated from a Loss on Ignition (LOI) test that measures the weight difference obtained by drying a sample of the unused adsorbent at 900° C. under an inert gas purge such as nitrogen for a period of time (e.g., 2 hours) sufficient to achieve a constant weight. The sample is first conditioned at 350° C. for 2 hours. The percentage of weight loss, based on the initial sample weight, is the LOI at 900° C. An increased LOI value may be achieved by equilibrating a fixed amount of adsorbent, having a lower LOI than desired, and a fixed amount of water in a sealed dessicator until equilibrium is established. The LOI value of an adsorbent may be decreased through drying at 200-350° C. under an inert gas purge or vacuum for a period of time (e.g., 2 hours).

It is recognized that LOI is an indirect or relative measurement of the adsorbent hydration level (or water content), as other volatile components (e.g., organic materials), typically on the order of 0.5% by weight, are also lost during the analysis. Therefore, the desired adsorbent LOI is simply that which corresponds to a water content from about 3% to about 5.5% by weight, and preferably from about 3.5% to about 4.5% by weight. The absolute amount of water in a zeolitic adsorbent sample can be determined by known analytical methods such as Karl Fischer (ASTM D1364). A desired water content is readily controlled/obtained by adjusting the final binderless adsorbent drying conditions (e.g., time and temperature) after the adsorbent is synthesized as discussed above.

During the use of the binderless adsorbent in the adsorptive separation of para-xylene (e.g., in a simulated moving bed mode of operation), it is generally desired to maintain the adsorbent water content in the ranges described above in order to obtain favorable performance characteristics in terms of adsorbent capacity and selectivity, as discussed previously. The adsorbent water content may be adjusted and/or maintained, if desired, through continuous or intermittent addition or injection of water into a suitable inlet stream, for example the feed stream and/or desorbent stream. According to one exemplary embodiment, the adsorbent water content or level of hydration is maintained by monitoring the water content in the extract and/or raffinate streams and adjusting the amount of water added to one or more inlet streams if and when necessary. For example, a representative range of water in either or both of these streams, corresponding to a desirable adsorbent water content (e.g., in the ranges given above), is from about 20 ppm by weight to about 120 ppm by weight. Often the desired water content in one or both of these outlet streams is from about 40 ppm to about 80 ppm by weight.

Although the adsorptive separation of para-xylene from other $C_8$ alkylaromatic compounds may be conducted in either the liquid phase or the vapor phase, predominantly liquid-phase operation is normally used. As discussed above, adsorption temperatures of less than about 175° C. (350° F.), for example from about 130° C. (270° F.) to about 165° C. (330° F.), are particularly advantageous when used with binderless adsorbents, such as those comprising small-crystallite-size zeolite X, to overcome mass transfer limitations, which prevent conventional adsorbents from exploiting the improved para-xylene adsorptive selectivity and adsorbent capacity at these temperatures. Adsorption conditions can also include a pressure in the range from about atmospheric pressure to about 600 psig, with pressures from about 1 barg (15 psig) to about 40 barg (580 psig) being typical. Desorption conditions often include substantially the same temperature and pressure as used for adsorption.

Separation of para-xylene is carried out by contacting a mixture of para-xylene and at least one other $C_8$ alkylaromatic hydrocarbon with an adsorbent, and under adsorption conditions, as described above. For example, a feed stream comprising the mixture of $C_8$ alkylaromatic hydrocarbons may be contacted with a bed of the adsorbent in order to selectively adsorb, in an adsorbed phase, the para-xylene, in preference to ortho-xylene, meta-xylene, and ethylbenzene. These other $C_8$ alkylaromatic components of the feed stream may selectively pass through the adsorption zone as a non-adsorbed phase.

Feed streams comprising mixtures of $C_8$ alkylaromatic hydrocarbons can be separated from various refinery process streams (e.g., reformate) including the products of separation units. Such separations are imprecise and the feed is therefore expected to contain limited amounts (e.g., less than 5 mol-%, and often less than 2 mol-%) of other compounds, such as $C_9$ alkylaromatic hydrocarbons. In most instances, the feed will be primarily $C_8$ alkylaromatic hydrocarbons and contain a total of less than 10 mol-%, typically less than 5 mol-%, and in some cases less than 1 mol-%, of other types of compounds. In one type of separation process, after the adsorptive capacity of the adsorbent is reached, the feed stream inlet flow to the adsorbent is stopped, and the adsorption zone is then flushed to remove a non-adsorbed phase, initially surrounding the adsorbent, from contact with the adsorbent. The adsorbed phase, enriched in the desired para-xylene, may be thereafter desorbed from the adsorbent pores by treating the adsorbent with a desorbent, normally comprising a cyclic hydrocarbon (e.g., an aromatic ring-containing hydrocarbon) such as toluene, benzene, indan, para-diethylbenzene, 1,4-diisopropylbenzene, or mixtures thereof. The same desorbent is commonly used for both (i) flushing the non-adsorbed phase into a raffinate stream comprising the desorbent and (ii) desorbing the adsorbed phase into an extract stream, also comprising the desorbent. Because the extract stream contains the adsorbed phase, which is enriched in para-xylene, the extract stream will also be enriched in para-xylene, relative to the feed stream, when considered on a desorbent-free basis.

As used herein, a "feed stream" is a mixture containing the desired extract component (para-xylene) and one or more raffinate components to be separated by the adsorptive separation process. A "feed mixture" (i.e., comprising "feed mixture components") therefore comprises the mixture of extract and raffinate components, such as a mixture of xylenes (ortho-xylene, meta-xylene, and para-xylene as discussed above) and ethylbenzene. The feed stream is an inlet stream to the adsorbent (e.g., in the form of one or more adsorbent beds) used in the process. An "extract component" is a compound or class of compounds that is selectively adsorbed by the adsorbent. A "raffinate component" is a compound or class of compounds that is less selectively adsorbed (or selectively rejected). A "desorbent" is generally any material capable of desorbing an extract component from the adsorbent, and a "desorbent stream" is an inlet stream to the adsorbent, which contains desorbent. A "raffinate stream" is an outlet stream from the adsorbent, in which a raffinate component is removed. The composition of the raffinate stream can vary from essentially 100% desorbent to essentially 100% raffinate components, with minor amounts one or more extract components. An "extract stream" is an outlet stream from the adsorbent, in which an extract component is removed. The composition of the extract stream can vary from essentially 100% desorbent to essentially 100% extract components, with minor amounts of one or more raffinate components.

Typically, at least some portion of the extract stream and the raffinate stream are purified (e.g., by distillation) to remove desorbent and thereby produce an extract product stream and a raffinate product stream. The "extract product stream" and "raffinate product stream" refer to products produced by the adsorptive separation process containing, respectively, an extract component and a raffinate component in higher concentration than present in the extract stream and the raffinate stream, respectively, and also in higher concentration than present in the feed stream.

The capacity of the adsorbent for adsorbing a specific volume of an extract component is an important characteristic, as increased capacity makes it possible to reduce the amount of adsorbent (and consequently the cost) needed to separate the extract component for a particular charge rate of feed mixture. Good initial capacity for the extract component, as well as total adsorbent capacity, should be maintained during actual use in an adsorptive separation process over some economically desirable life.

The rate of exchange of an extract component (para-xylene) with the desorbent can generally be characterized by the width of the peak envelopes at half intensity obtained from plotting the composition of various species in the adsorption zone effluent obtained during a pulse test versus time. The narrower the peak width, the faster the desorption rate. The desorption rate can also be characterized by the distance between the center of the tracer peak envelope and the disappearance of an extract component which has just been desorbed. This distance is time dependent and thus a measure of the volume of desorbent used during this time interval. The tracer is normally a relatively non-adsorbed compound which moves through an adsorbent column faster than the materials to be separated.

Selectivity ($\beta$), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope (or reference point). The selectivity corresponds to the ratio of the two components in the adsorbed phase divided by the ratio of the same two components in the non-adsorbed phase at equilibrium conditions. Selectivity may therefore be calculated from:

$$\text{Selectivity} = (\text{wt-\%}\ C_A/\text{wt-\%}\ D_A)/(\text{wt-\%}\ C_U/\text{wt-\%}\ D_U)$$

where C and D are two components of the feed mixture represented in weight percent and the subscripts A and U represent the adsorbed and non-adsorbed phases, respectively. The equilibrium conditions are determined when the feed passing over a bed of adsorbent does not change composition, in other words, when there is no net transfer of material occurring between the non-adsorbed and adsorbed phases. In the equation above, a selectivity larger than 1.0 indicates preferential adsorption of component C within the adsorbent. Conversely, a selectivity less than 1.0 would indicate that component D is preferentially adsorbed leaving an non-adsorbed phase richer in component C and an adsorbed phase richer in component D.

For a selectivity of two components approaching 1.0, there is no preferential adsorption of one component by the adsorbent with respect to the other (i.e., they are both adsorbed to about the same degree with respect to each other). As selectivity deviates from 1.0, there is an increasingly preferential adsorption by the adsorbent for one component with respect to the other. Selectivity can be expressed not only for one feed stream compound relative to another (e.g., para-xylene to meta-xylene selectivity) but can also be expressed between any feed stream compound and the desorbent (e.g., para-xylene to para-diethylbenzene selectivity).

While separation of an extract component from a raffinate component is theoretically possible when the adsorbent selectivity for the extract component with respect to the raffinate component is only slightly greater than 1, it is preferred that this selectivity is at least 2 for process economic considerations. Analogous to relative volatility in fractional distillation, the higher the selectivity, the easier the adsorptive separation is to perform. Higher selectivities directionally permit a smaller amount of adsorbent to be used, just as higher relative volatilities require fewer theoretical stages of distillation (and a smaller column) to carry out a given distillation separation for a given feed.

The desorbent for an adsorptive separation process must be judiciously selected to satisfy several criteria. The desorbent should ideally have sufficient strength (i.e., be adsorbed strongly enough) to displace an extract component from the adsorbent at a reasonable mass flow rate, without being so strongly adsorbed as to prevent an extract component from displacing the desorbent in a following adsorption cycle. In terms of the selectivity, it is preferred that the adsorbent be more selective for the extract component with respect to a raffinate component than it is for the desorbent with respect to the raffinate component. Additionally, the desorbent must be compatible with both the adsorbent as well as the feed mixture. In particular, the desorbent should not adversely affect the desired selectivity of the adsorbent for an extract component with respect to a raffinate component. Additionally, the desorbent should be essentially chemically inert with respect to extract and raffinate components, as both the extract stream and the raffinate stream are typically removed from the adsorbent in admixture with desorbent. Any chemical reaction involving desorbent and an extract component or a raffinate component would complicate or possibly prevent product recovery.

A performance parameter to be considered for the desorbent is therefore its rate of exchange for the extract component of the feed or, in other words, the relative rate of desorption of the extract component. This parameter relates directly to the amount of desorbent that must be used in an adsorptive separation process to desorb the extract component from the adsorbent. Faster rates of exchange reduce the amount of desorbent needed and therefore reduce operating costs associated with larger desorbent-containing process streams, including the separation and recycle of desorbent from these streams. A desorbent selectivity of 1 or slightly lower with respect to an extract component helps ensure that all the extract component is desorbed with a reasonable flow rate of desorbent, and also that extract components can displace desorbent in a subsequent adsorption step.

Moreover, since both the raffinate stream and the extract stream normally contain desorbent, the desorbent should also be easily separable from the mixture of extract and raffinate components introduced in the feed stream. Without a method of separating desorbent in the extract stream and the raffinate stream, the concentration of an extract component in the extract product and the concentration of a raffinate component in the raffinate product would not be commercially favorable, nor would the desorbent be available for reuse in the process. At least a portion of the desorbent is therefore normally recovered from the extract stream and the raffinate stream of an adsorptive separation process by distillation or evaporation, although other separation methods such as reverse osmosis could also be used alone or in combination with distillation or evaporation. In this regard, the desorbent is generally a "light" or "heavy" desorbent that is easily separable, as a distillation overhead or bottoms product, respectively, from the $C_8$ alkylaromatic hydrocarbons in the extract stream and raffinate stream of a para-xylene adsorptive separation process.

A "pulse test" may be employed to test adsorbents with a particular feed mixture and desorbent to measure such adsorbent properties as adsorptive capacity, selectivity, resolution, and exchange rate. A representative pulse test apparatus includes a tubular adsorbent chamber of approximately 70 cubic centimeters (cc) in volume and having inlet and outlet portions at opposite ends of the chamber. The chamber is equipped to allow operation at constant, predetermined temperature and pressure. Quantitative and qualitative analytical equipment such as refractometers, polarimeters and chromatographs can be attached to an outlet line of the chamber and used to detect quantitatively and/or determine qualitatively one or more components in the effluent stream leaving the adsorbent chamber. During a pulse test, the adsorbent is first filled to equilibrium with a particular desorbent by passing the desorbent through the adsorbent chamber. A small volume or pulse of the feed mixture, which may be diluted with desorbent, is injected by switching the desorbent flow to the feed sample loop at time zero. Desorbent flow is resumed, and the feed mixture components are eluted as in a liquid-solid chromatographic operation. The effluent can be analyzed on-stream or, alternatively, effluent samples can be collected periodically and analyzed separately (off-line) and traces of the envelopes of corresponding component peaks plotted in terms of component concentration versus quantity of effluent.

Information derived from the pulse test can be used to determine adsorbent void volume, retention volume for an extract component or a raffinate component, selectivity for one component with respect to the other, stage time, the resolution between the components, and the rate of desorption of an extract component by the desorbent. The retention volume of an extract component or a raffinate component may be determined from the distance between the center of the peak envelope of an extract component or a raffinate component and the peak envelope of a tracer component or some other known reference point. It is expressed in terms of the volume in cubic centimeters of desorbent pumped during the time interval corresponding to the distance between the peak envelopes.

Retention volumes for good candidate systems fall within a range set by extrapolation to commercial designs. A very small retention volume indicates there is little separation between the two components (i.e., one component is not adsorbed strongly enough). Large extract component retention volumes indicate it is difficult for the desorbent to remove the retained extract component.

Conventional apparatuses employed in static bed fluid-solid contacting may be used in adsorptive separation processes incorporating a binderless adsorbent, as described above. The adsorbent may be employed in the form of a single fixed bed which is alternately contacted with the feed stream and desorbent stream. The adsorbent may therefore be used in a single static bed that is alternately subjected to adsorption and desorption steps in a non-continuous (e.g., batch) process. A swing bed mode of operation is also possible, in which multiple beds are periodically used for a given operation or step. Alternatively, a set of two or more static beds may be employed with appropriate piping/valves to allow continual passage of the feed stream through any one of a number of adsorbent beds while the desorbent stream is passed through one or more of the other beds in the set. The flow of the feed stream and desorbent may be either upward or downward through the adsorbent.

A countercurrent moving bed mode of operation provides another potential mode of operation, in which a stationary concentration profile of the feed mixture components can be achieved, allowing for continuous operation with fixed points of feed stream and desorbent stream introduction, as well as extract stream and raffinate stream withdrawal. Countercurrent moving bed or simulated moving bed countercurrent flow systems have a much greater separation efficiency than fixed adsorbent systems and are therefore very often used for commercial-scale adsorptive separations. In a simulated moving bed process, the adsorption and desorption are normally carried out continuously in a simulated moving bed mode, allowing both continuous production (withdrawal) of an extract stream and a raffinate stream (both outlet streams), as well as the continual use (input) of a feed stream and a desorbent stream (both inlet streams).

The operating principles and step sequence of a simulated moving bed flow system are described in U.S. Pat. Nos. 2,985,589, 3,310,486, and 4,385,993, incorporated by reference herein for their teachings with respect to simulated moving bed flow systems. In such systems, it is the progressive movement of multiple access points along an adsorbent chamber that simulates the movement of adsorbent (opposite the liquid access point movement) contained in one or more chambers. Typically only four of the many (16 to 24 or more) access lines to the chamber(s) are active at any one time, for carrying the feed stream, the desorbent stream, the raffinate stream, and the extract stream. Coincident with this simulated movement (e.g., upward movement) of the solid adsorbent is the movement (e.g., downward movement) of fluid occupying the void volume of the packed bed of adsorbent. The circulation of this fluid (e.g., liquid) flow may be maintained using pump. As an active liquid access point moves through a cycle, that is, through each adsorbent bed contained in one or more chambers, the chamber circulation pump generally provides different flow rates. A programmed flow controller may be provided to set and regulate these flow rates.

The active access points effectively divide the adsorbent chamber into separate zones, each of which has a different function. Three separate operational zones are generally present for the process to take place, although, in some cases, an optional fourth operation zone is used. The zone numbers used in the following description of a simulated moving bed process correspond to those illustrated in U.S. Pat. No. 3,392,113 and 4,475,954, also incorporated by reference herein with respect to their teachings regarding simulated moving bed operation.

The adsorption zone (zone 1) is defined as the adsorbent located between the inlet feed stream and the outlet raffinate stream. In this zone, the feed mixture contacts the adsorbent, an extract component is adsorbed, and a raffinate stream is withdrawn. The general flow through zone 1 is from the feed stream which passes into the zone to the raffinate stream which passes out of the zone, and the flow in this zone is normally considered to be in a downstream direction when proceeding from the inlet feed stream to the outlet raffinate stream.

Immediately upstream, with respect to fluid flow in zone 1, is the purification zone (zone 2). The purification zone is defined as the adsorbent between the outlet extract stream and the inlet feed stream. The basic operations in this zone are the displacement from the non-selective void volume of the adsorbent of any raffinate component carried into zone 2 and the desorption of any raffinate component adsorbed within the selective pore volume of the adsorbent or adsorbed on the surfaces of the adsorbent particles. Purification is achieved by passing a portion of the extract stream leaving zone 3 into zone 2 at its upstream boundary, the extract outlet stream, to effect the displacement of raffinate components. The flow in zone 2 is in a downstream direction from the extract outlet stream to the feed inlet stream. This material then joins the feed stream and flows through zone 1.

Immediately upstream of zone 2 with respect to the fluid flowing in zone 2 is the desorption zone (zone 3). The desorption zone is defined as the adsorbent between the inlet desorbent stream and the outlet extract stream. The function of the desorbent zone is to allow a desorbent which passes into this zone to displace the extract component which was adsorbed in the adsorbent during a previous contact with the feed mixture in zone 1, in a prior cycle of operation. The flow of fluid in zone 3 is essentially in the same direction as that in zones 1 and 2.

In some instances, an optional buffer zone (zone 4) may be utilized. This zone, defined as the adsorbent between the outlet raffinate stream and the inlet desorbent stream, if used, is located immediately upstream with respect to the fluid flow into zone 3. Zone 4 can be utilized to conserve the amount of desorbent needed for desorption, since a portion of the raffinate stream which is removed from zone 1 can be passed into zone 4 to displace desorbent from that zone out into the desorption zone. Zone 4 will contain enough adsorbent so that raffinate components in the raffinate stream passing from zone 1 into zone 4 can be prevented from passing into zone 3 and thereby contaminating the extract stream withdrawn from zone 3. If a fourth operational zone is not utilized, the raffinate stream passed from zone 1 to zone 4 must be carefully monitored in order that the flow directly from zone 1 to zone 3 can be stopped when there is an appreciable quantity of raffinate components present in the raffinate stream passing from zone 1 into zone 3 so that the extract outlet stream is not contaminated.

A cyclic advancement of the input (feed and desorbent) streams and output (extract and raffinate) streams through fixed beds of adsorbent, to provide a continuous process performed in a simulated moving bed mode, can be accomplished by utilizing a manifold system in which the valves in the manifold are operated in a manner which effects the shifting of the input and output streams thereby providing a flow of fluid with respect to solid adsorbent in a simulated countercurrent manner. Another type of operation which can simulate countercurrent flow of solid adsorbent involves the use of a rotating valve in which the input and output streams are each directed by the valve to one of the many lines connected to the adsorbent chamber and by which the location at which the input feed stream, output extract stream, input desorbent stream, and output raffinate stream enter or leave the chamber are advanced in the same direction along the adsorbent bed. Both the manifold arrangement and rotary disc valve are known in the art. A multiple valve apparatus is described in detail in U.S. Pat. No. 4,434,051. Rotary disc valves which can be utilized in this operation are described in U.S. Pat. Nos. 3,040,777, 4,632,149, 4,614,204, and 3,422,848. These patents disclose a rotary type valve in which the suitable advancement of the various input and output streams from fixed sources can be achieved without difficulty.

In many instances, one operational zone of a simulated moving bed process will contain a much larger quantity of adsorbent than another operational zone. For instance, in some operations the buffer zone can contain a minor amount of adsorbent compared to the adsorbent present in the adsorption and purification zones. As another example, in instances in which a desorbent is used that easily desorbs the extract component from the adsorbent, a relatively small amount of adsorbent will be needed in the desorption zone compared to the amount of adsorbent needed in the buffer zone, adsorption zone, purification zone or all of these zones. Also, it is not required that the adsorbent be located in a single chamber (i.e., column or vessel), and often two adsorbent chambers (e.g., each provided with 12 access lines) are used. Additional chambers are also contemplated.

Normally at least a portion of the output extract stream will pass to a separation process such as a fractionation column, in order to recover a portion of the desorbent (e.g., for recycle to the adsorptive separation process as a desorbent recycle stream) and produce a purified extract product stream (e.g., containing a reduced amount of desorbent). Preferably at least a portion of the output raffinate stream will also pass to a separation process, in order to recover another portion of the desorbent (e.g., also for recycle to the adsorptive separation process) and a raffinate product stream (e.g., also containing a reduced concentration of desorbent). In large-scale petrochemical units, essentially all of the desorbent is recovered for reuse. The design of fractional distillation facilities for this recovery will be dependent on the materials being separated, the desorbent composition, etc.

Another type of a simulated moving bed flow system suitable for use in adsorptive separation processes described above is a co-current high efficiency simulated moving bed process described in U.S. Pat. Nos. 4,402,832 and 4,478,721, incorporated by reference herein with respect to their teachings of this alternative mode of operation. This process has advantages in terms of energy efficiency and reduced capital costs, in cases where products of slightly lower purity are acceptable to the producer.

The scale of adsorptive separation units for the purification of para-xylene can vary from those of pilot plant scale (see, for example, U.S. Pat. No. 3,706,812) to commercial scale and can range in produce flow rates from as little as a few milliliters an hour to many hundreds of cubic meters per hour.

Overall, aspects of the invention are directed to the exploitation of the unique properties of binderless adsorbents for use in adsorptive separations, and particularly in commercial simulated moving bed operations. In view of the present disclosure, it will be seen that several advantages may be achieved and other advantageous results may be obtained. Those having skill in the art, with the knowledge gained from the present disclosure, will recognize that various changes could be made in the above adsorbent compositions, and processes using these compositions, without departing from the scope of the present disclosure. The chemical processes, mechanisms, modes of interaction, etc. used to explain theoretical or observed phenomena or results, shall be interpreted as illustrative only and not limiting in any way the scope of the appended claims.

The following examples are set forth as representative of the present invention. These examples are not to be construed as limiting the scope of the invention as these and other equivalent embodiments will be apparent in view of the present disclosure and appended claims.

EXAMPLE 1

Synthesis of Binderless Adsorbent Particles Comprising Small-Crystallite-Size Zeolite X Small-crystallite-size Zeolite X powder, made according to procedures described herein, was combined with a known amount of commercially available kaolin and water to form an extrudable paste, which was then extruded to form composite pellets with 50-90% small-crystallite-size zeolite X in kaolin. The composite was then dried at 100° C. and finally calcined at >600° C. in order to convert the binder kaolin to meta-kaolin. The binder meta-kaolin was then converted to zeolite X by hydrothermal treatment in <5 wt % NaOH solution at >2 Na/Al (from meta-kaolin) for up to 10 hours with mild agitation. Although the kaolin clay had a silica to alumina molar ratio of 2.0, it was found that this ratio in the converted zeolite X could be increased by adding a silica source, such as colloidal silica sol, silicic acid, alkali metal silicate, silica gel, or reactive particulate silica, during the caustic digestion of the meta-kaolin. The silica source could be added to the mixture to be formed, to the alkaline reaction medium or both. The resulting binderless adsorbent particles therefore had both prepared and converted portions of zeolite X having a silica to alumina molar ratio of about 2.5. The prepared portion of zeolite X was small-crystallite-size. The adsorbent particles were ion-exchanged in a column as described herein, in order to convert the sodium form of zeolite X to the barium/potassium form, having over 99% of the ion exchange sites replaced with a combination of barium and potassium

EXAMPLE 2

Selectivity Testing

Figure 2:
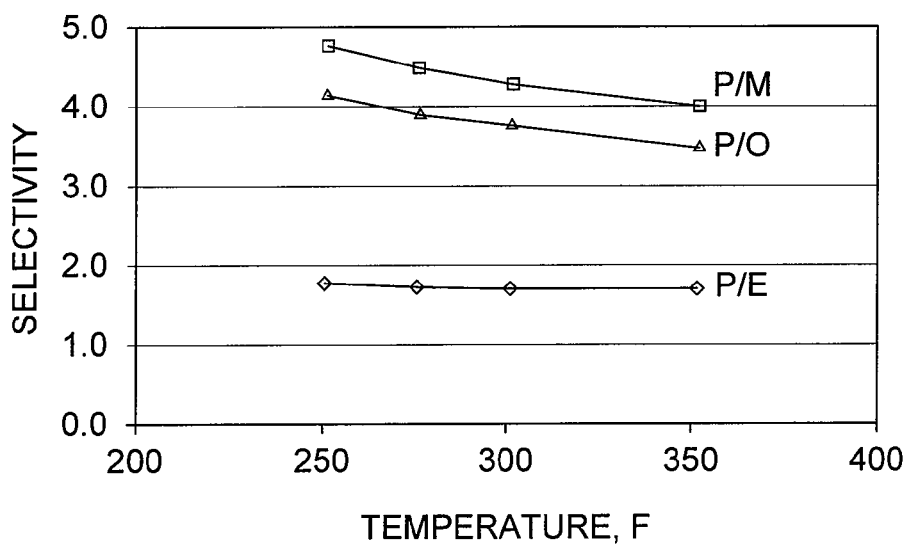
FIG. 2 shows the selectivities of feed mixture components (i.e., the para-xylene/meta-xylene selectivity, "P/M"; the para-xylene/ortho-xylene selectivity, "P/O"; and the para-xylene/ethylbenzene selectivity, "P/E"), as a function of temperature, obtained from a pulse test using an adsorbent comprising zeolite X.

A conventional adsorbent comprising zeolite X exchanged with barium and potassium, and having an LOI of 6 wt-%, was evaluated in the adsorptive separation of para-xylene. A standard pulse test as described above was performed by first loading the adsorbent in a 70 cc column under the desorbent para-diethylbenzene. A feed pulse containing equal quantities of ethylbenzene and each of the three xylene isomers, together with a normal nonane ($n$-$C_9$) tracer, was injected. Pulse tests were performed at various column temperatures in the range from 121° C. to 177° C. (250° F. to 350° F.) to examine the effect of temperature on selectivity. The para-xylene selectivities were determined from the component peaks obtained from each of these pulse tests, and the results are shown in FIG. 2.

The results show that the para-xylene/meta-xylene selectivity, "P/M," and the para-xylene/ortho-xylene selectivity, "P/O," increase at lower adsorption temperatures, while the para-xylene/ethylbenzene selectivity, "P/E," varies little with respect to temperature. This demonstrates that lower adsorptive separation temperatures are favored from a thermodynamic equilibrium (although not necessarily from a kinetic) standpoint.

EXAMPLE 3

Capacity Testing

Figure 3:
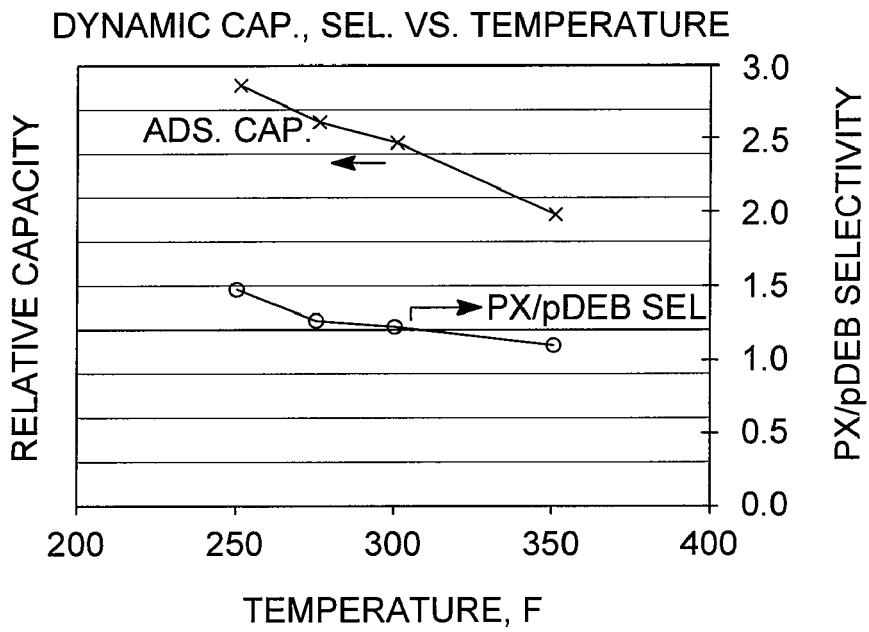
FIG. 3 shows the capacity of an adsorbent comprising zeolite X, as well as the para-xylene/para-diethylbenzene selectivity, "PX/pDEB Sel," as a function of temperature, obtained from a breakthrough (or dynamic) test.

A chromatographic separation (dynamic capacity or breakthrough test) was performed using a conventional adsorbent as described in Example 2. A column containing 70 cc of the adsorbent, initially loaded under para-diethylbenzene, was charged with a sample feed mixture containing ortho-xylene, meta-xylene, para-xylene, and ethylbenzene. Breakthrough tests were performed at various column temperatures in the range from 121° C. to 177° C. (250° F. to 350° F.) to examine the effect of temperature on adsorbent capacity and para-xylene/para-diethylbenzene selectivity, "PX/pDEB Sel," and the results are shown in FIG. 3. The results further confirm that lower adsorptive separation temperatures are favorable, in terms of total adsorbent capacity, without adversely affecting the para-xylene/desorbent selectivity.

EXAMPLE 4

Mass Transfer Rate

Figure 4:
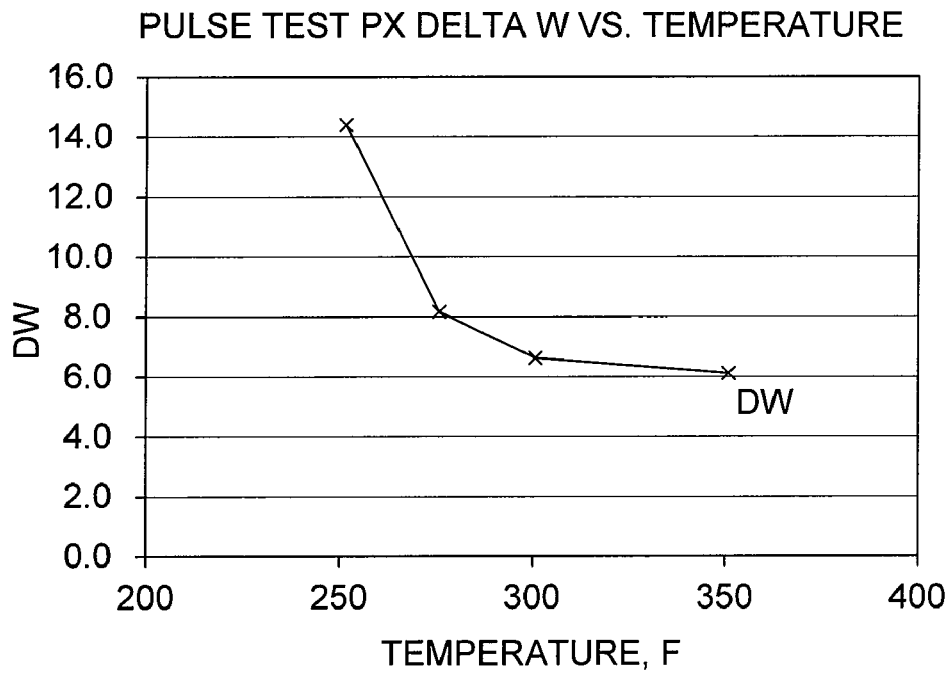
FIG. 4 shows the "DW" or "Delta W," namely the half width of the para-xylene peak (i.e., peak envelope width at half intensity), minus the half width of normal nonane (n-$C_9$) tracer peak, as a function of temperature, obtained from a pulse test using an adsorbent comprising zeolite X.

Using the data obtained from pulse tests as described in Example 2, the "DW" or "Delta W," namely the half width of the para-xylene peak (i.e., peak envelope width at half intensity), minus the half width of normal nonane tracer peak (to account for dispersion), was determined as a function of temperature. The results are shown in FIG. 4 and indicate that mass transfer limitations become significant in conventional para-xylene adsorptive separation processes at temperatures below about 177° C. (350° F.).

EXAMPLE 5

Figure 5:
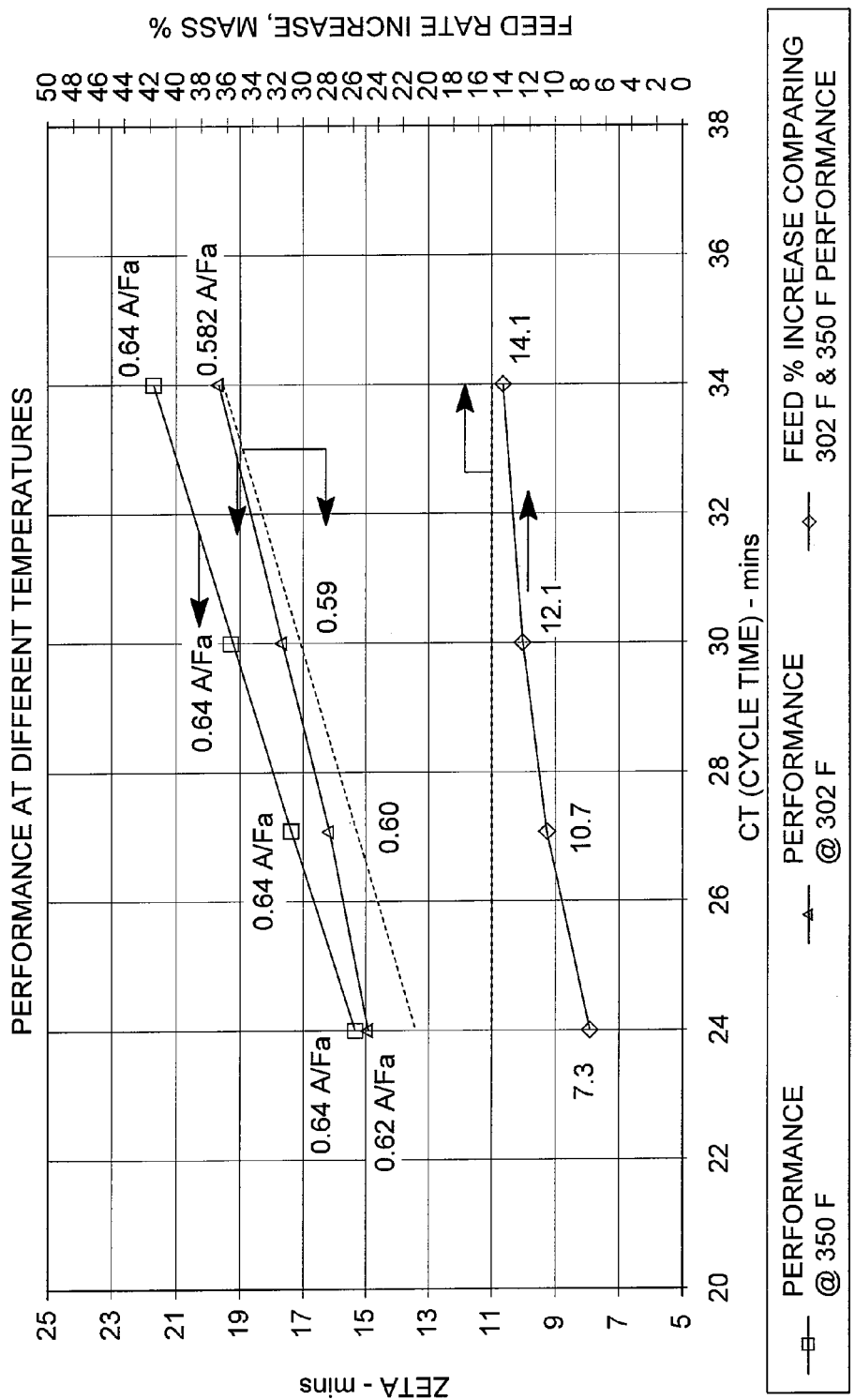
FIG. 5 shows the performance of a para-xylene adsorptive separation process operating in a simulated moving bed mode at temperatures of 150° C. (302° F.) and 177° C. (350° F.).

Adsorptive Separation of Para-Xylene in Simulated Moving Bed Mode, Temperature Effects The performance of a conventional adsorbent, as described in Example 2, in the adsorptive separation of para-xylene in a pilot plant operating in a simulated moving bed mode is illustrated in FIG. 5. At all conditions analyzed, the total para-xylene recovered in the extract stream was about 95 wt-%. Measured performance parameters at 150° C. (302° F.) are shown (solid square symbols), compared to those at 177° C. (350° F.) (solid triangular symbols), as a function of the process cycle time. In all cases, the value of zeta (Y-axis, left side) at the lower temperature was below the corresponding value at the higher temperature, indicating that higher para-xylene productivity was achieved at lower operating temperature, due to the improved para-xylene adsorption selectivity and adsorbent capacity, as confirmed in the pulse and breakthrough tests, described in Examples 2 and 3.

The zeta value is a measure of selective pore volume required for processing a unit volumetric rate of para-xylene containing feed. Lower zeta values therefore directionally indicate higher throughput or productivity. In particular, the zeta value is calculated as the product of $A/F_a$ and $\theta$, where A is the rate of simulated circulation of the selective adsorbent pore volume, $F_a$ is the volumetric rate of the feed stream containing the mixture of $C_8$ alkylaromatic hydrocarbons, and $\theta$ is the cycle time. The quantity $A/F_a$ is shown in FIG. 5 for each combination of cycle time and temperature tested. The near convergence, at low cycle times, of the curves generated at high and low temperature operation indicates that the low temperature performance advantages become less pronounced as cycle time is reduced (and as productivity or zeta is maximized).

This barrier to obtaining even higher productivity, observed in practice, is due to mass transfer limitations. The bottom curve in FIG. 5 (open diamonds) illustrates the impact of mass transfer limitations on productivity, in terms of the possible feed stream volumetric rate increase (Y-axis, right side) that is obtained by reducing operating temperature from 177° C. (350° F.) to 150° C. (302° F.) at each cycle time. For a cycle time of 34 minutes, for example, the benefit of lower operating temperature translates into an approximately 14% increase in the volumetric rate at which the $C_8$ alkylaromatic feed stream that can be processed. The productivity advantage, however, decreases to only about 7% for a cycle time of 24 minutes, as a result of mass transfer limitations. The dashed lines in FIG. 5, in contrast, illustrate the para-xylene adsorptive separation performance parameters and feed productivity advantages that are theoretically possible in the absence of mass transfer limitations.

The laboratory and pilot plant scale studies described in Examples 2-5 therefore illustrate that, while lower operation temperature results in significant advantages in adsorbent capacity, adsorption selectivity, and increased liquid density per unit volume of adsorbent, it also reduces the mass transfer rate. As a result, it is difficult to take full advantage of the thermodynamically favorable operating regime, at temperatures ranging from about 130° C. (270° F.) to about 165° C. (330° F.), in the adsorptive separation of para-xylene from a relatively impure mixture of $C_8$ alkylaromatic hydrocarbons. As is shown in FIG. 5, with decreasing cycle time, the productivity advantage of 150° C. (300° F.) operation decreases in the case of conventional adsorbents.

EXAMPLE 6

Adsorptive Separation of Para-Xylene in Simulated Moving Bed Mode, Bed Concentration Profiles The feed mixture component and desorbent concentration profiles for each of 24 adsorbent beds, obtained during the adsorptive separation of para-xylene in a pilot plant operating in a simulated moving bed mode using a conventional adsorbent (as described in Example 2), were evaluated. A liquid composition "survey" (i.e., analysis of the liquid composition in each bed) was performed during steady state operation at 150° C. (302° F.) and about 95% recovery of para-xylene in the extract stream. The concentration profiles were obtained using a cycle time of 34 minutes and 24 minutes, respectively. These survey results again confirmed that significant mass transfer limitations prevent full realization of the more favorable para-xylene adsorption selectivity and adsorbent capacity at this temperature. The adverse effects of limited mass transfer are manifested in a more dispersed para-xylene front in the adsorption zone (zone I, as discussed above). The theoretical productivity increase associated with low temperature operation cannot be realized, using a conventional adsorbent, as cycle time is reduced to more commercially desirable values (e.g., 24-34 minutes).

A High Resolution Scanning Electron Microscopy (HR SEM) micrograph of a binderless adsorbent comprising zeolite X illustrated that the zeolite X crystallites present the main diffusion path that limits the mass transfer rate.

EXAMPLE 7

Figure 6:
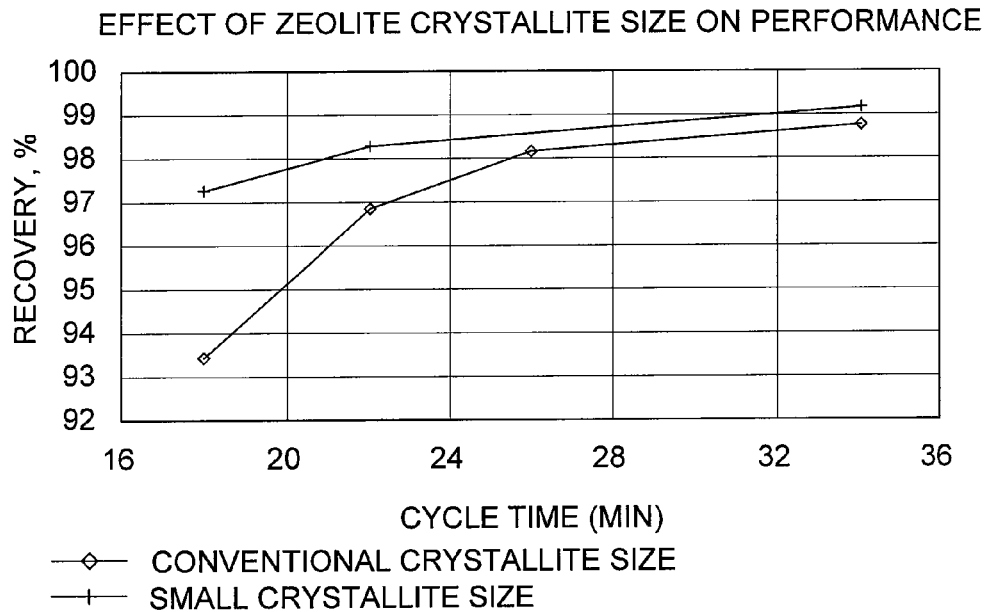
FIG. 6 shows the effect of cycle time on para-xylene recovery, in a para-xylene adsorptive separation process operating in a simulated moving bed mode, for an adsorbent comprising conventional zeolite X crystallites and another adsorbent comprising zeolite X having a reduced crystallite size.
Figure 7:
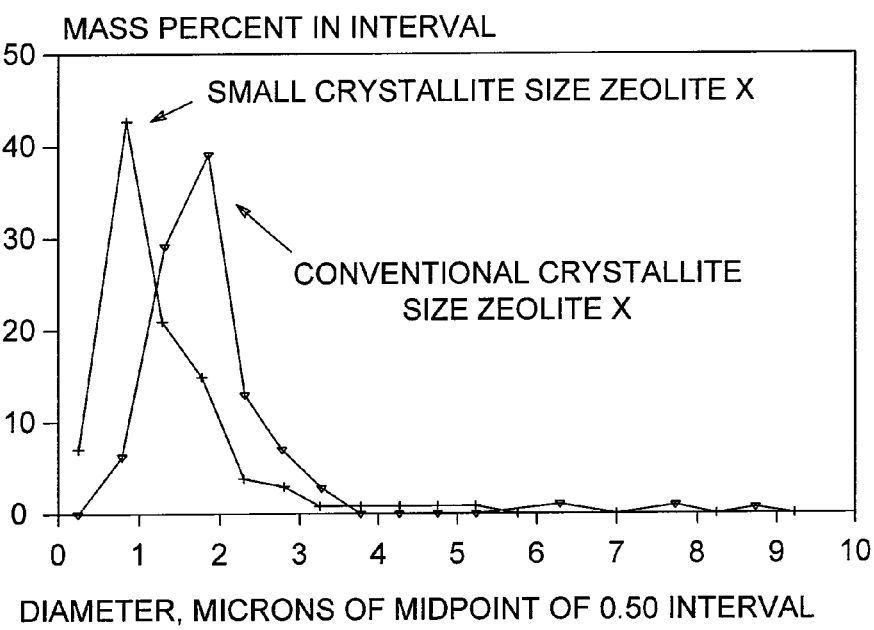
FIG. 7 shows the size distribution of both conventional zeolite X crystallites and zeolite X crystallites having a reduced size.

Reducing Zeolite X Crystallite Size in Adsorbents to Improve Adsorptive Separation of Para-Xylene in Simulated Moving Bed Mode FIG. 6 compares the performance of a conventional adsorbent comprising zeolite X, having an average crystallite of size 1.8-2.0 microns, to an adsorbent comprising zeolite X, having an average crystallite size of 1.4 microns. The zeolite X crystallite size distributions, for a representative conventional zeolite X sample and another sample having the reduced crystallite size, such as those used in the tested adsorbents, are illustrated in FIG. 7, with the average crystallite size for the conventional zeolite X being 1.8-2.0 microns. While maintaining all other conditions constant in a para-xylene adsorptive separation process operating in a simulated moving bed mode, the adsorbent comprising the zeolite X having a reduced crystallite size allowed for a higher overall para-xylene recovery. The advantages associated with reducing zeolite X crystallite size, and particularly the associated, improved mass transfer became more pronounced as cycle time was reduced, for the reasons discussed above, and as demonstrated in FIG. 6.

Thus, the reduction in zeolite X crystallite size in adsorbents provided a shortened mass transfer path, and consequently an improved mass transfer rate. This has important commercial implications, as para-xylene producers strive to improve productivity by reducing cycle time, in adsorptive separation processes operating in simulated moving bed mode, to below the standard, 34-minute operating parameter. For example, many commercial operations are conducted using 30- or even 27-minute cycle times.

In these cases, the use of adsorbents comprising small-crystallite-size zeolite X or nano-size zeolite X is especially advantageous in overcoming mass transfer rate limitations, particularly observed for operating temperatures of less than about 175° C. (350° F.). Small-crystallite-size zeolite X has been synthesized with average crystallite sizes in the range from about 0.5 microns (500 nanometers) to about 1.4 microns, which allows for optimization of the zeolite crystallite size for a given application, and consequently the adsorbent formulation and overall process.

EXAMPLE 8

Selectivities and Capacity of Binderless Adsorbents, Temperature Effects

Figure 8:
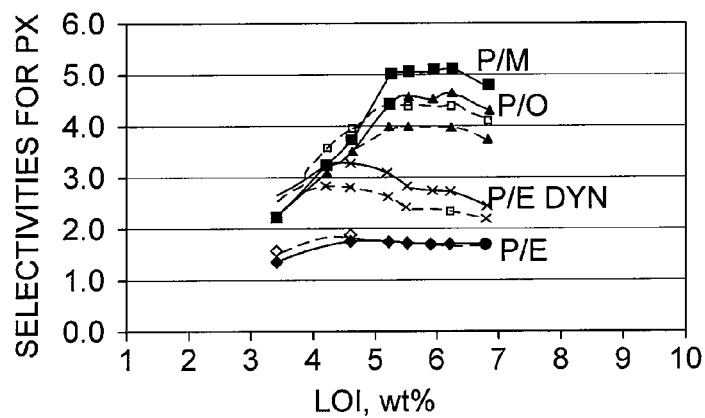
FIG. 8 shows, for a binderless adsorbent, a comparison of the para-xylene/meta-xylene selectivity, "P/M"; the para-xylene/ortho-xylene selectivity, "P/O"; and the para-xylene/ethylbenzene selectivity, "P/E," as a function of the loss on ignition (LOI), measured at temperatures of 150° C. (302° F.) and 177° C. (350° F.) using a pulse test, with P/E also being measured using a dynamic or breakthrough test (P/E dyn).
Figure 9:
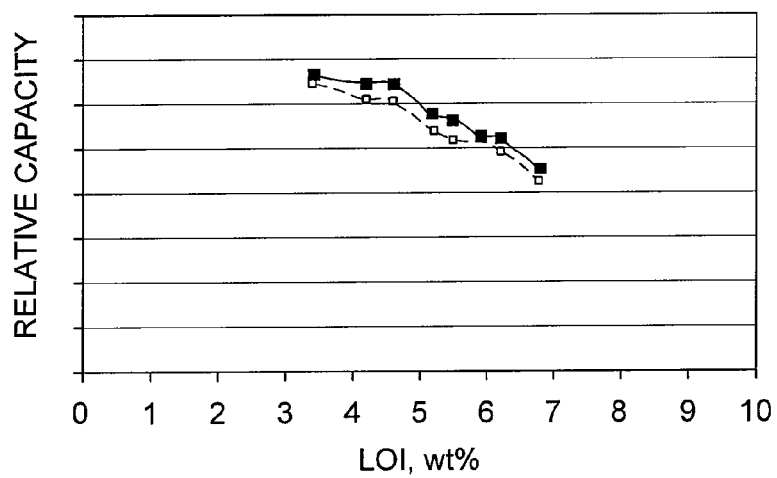
FIG. 9 shows, for a binderless adsorbent, a comparison of adsorbent capacity, measured at temperatures of 150° C. (302° F.) and 177° C. (350° F.) using a pulse test.

FIG. 8 illustrates the para-xylene/meta-xylene ("P/M"), para-xylene/ortho-xylene ("P/O"), and para-xylene/ethylbenzene ("P/E" or "P/E dyn") selectivity advantages at 150° C. (302° F.), compared to 177° C. (350° F.), at varying adsorbent hydration levels (or varying LOI values, as discussed above). The selectivity values P/M (squares), P/O (triangles), and P/E (diamonds) were obtained from a standard pulse test as described in Example 2, while the selectivity values P/E dyn (asterisks) were obtained from a dynamic or breakthrough test as described in Example 3. FIG. 9 illustrates the overall adsorbent capacity measured during these tests. For both FIGS. 8 and 9, data points obtained at the lower temperature are joined by solid lines, while data points obtained at the higher temperature are joined by dashed lines.

The data in FIGS. 8 and 9 further illustrate the advantages of lower temperature operation, in this case using binderless adsorbents. The para-xylene selectivity with respect to other xylene isomers and ethylbenzene can be significantly increased (e.g., on the order of 15%-20%) by reducing the operating or adsorption temperature, based on both the pulse and breakthrough test results at 150° C. (302° F.) and 177° C. (350° F.). Moreover, the adsorbent capacity is increased at lower temperature operation. These advantages associated with lower temperature operation can be more fully exploited as a result of the improved mass transfer and higher capacity associated with the binderless adsorbents described herein, and particularly, for example, comprising at least a portion of small-crystallite-size zeolite X.

EXAMPLE 9

Pulse and breakthrough (or dynamic) tests were carried out as described in Examples 2 and 3, respectively, using a conventional adsorbent comprising bound, barium-exchanged zeolite X and a binderless adsorbent, as described herein, comprising substantially all barium-exchanged zeolite X. The conventional adsorbent had an LOI value of 6% by weight, compared to 4.6% by weight for the binderless adsorbent. The data obtained from the tests included the para-xylene capacity (PX Cap), the total adsorbent capacity (Total Cap), and the para-xylene selectivities with respect to (i) para-diethylbenzene desorbent (PX/pDEB), (ii) ethylbenzene (PX/EB), (iii) ortho-xylene (PX/OX), and (iv) meta-xylene (PX/MX).

Also, the para-xylene mass transfer rate (Rate) was calculated from the breakthrough test data as the "adsorption breakthrough slope," described in U.S. Pat. No. 4,886,929, incorporated by reference herein with respect to its teaching of the calculation of this quantity (as a volume), which was divided by the volumetric flow rate used to generate the para-xylene peak, in order to obtain units of time. An additional indicator of mass transfer rate, namely the desorbent volume corresponding to the half width of the para-xylene peak (i.e., peak envelope width at half intensity, HW), generated from the pulse test, was also determined.

Data obtained from these tests are shown in Table 1.

TABLE 1

Pulse and Breakthrough Testing of Conventional and Binderless Adsorbents

| Ads | LOI wt % | PX Cap | Total Cap | Rate (sec) | HW (ml) | PX/ pDEB | PX/ EB | PX/ OX | PX. MX | % PX over ADS-27 |
|---|---|---|---|---|---|---|---|---|---|---|
| Conventional | 6 | 3.2 | 10.59 | 502 | 13.93 | 1.42 | 2.17 | 4.03 | 3.74 | — |
| Binderless | 4.6 | 4.12 | 12.44 | 664 | 15.35 | 1.82 | 2.60 | 4.27 | 3.74 | 28% |

As shown in Table 1, the binderless adsorbent exhibits improved para-xylene selectivities, para-xylene capacity, and total adsorbent capacity, relative to the conventional, bound adsorbent comprising zeolite X. The overall improvement in para-xylene capacity of about 28% over the conventional adsorbent is attributed to the ability of the binderless adsorbent to perform the para-xylene adsorptive separation at a lower water level (corresponding to the lower LOI value). The conventional, bound adsorbent cannot similarly function at this lower water level due to significant problems associated with mass transfer and selectivity.

The mass transfer rate of the binderless adsorbent, operating at a lower LOI value) is somewhat reduced relative to the conventional adsorbent, based on the "Rate" and "HW" values in Table 1. However, modification of the binderless adsorbent to incorporate small-crystallite-size zeolite X or even nano-size zeolite X (e.g., as a prepared portion and/or bound portion of zeolite X, as discussed previously) would be expected to overcome this mass transfer deficit.

EXAMPLE 10

The conventional and binderless adsorbents described in Example 9 were evaluated in the adsorptive separation of para-xylene in a pilot plant operating in a simulated moving bed mode. Table 2 provides the measured water content of these adsorbents using the Karl Fischer (ASTM D1364) analysis (KF Water %), as well as the following pilot plant operating parameters measured for different operational periods (1-5) under steady-state conditions: the cycle time, the quantity $A/F_a$ as defined in Example 5, the para-xylene purity (PX purity, %), and the para-xylene recovery (PX recovery, %).

TABLE 2

Testing of Conventional and Binderless Adsorbents in Simulated Moving Bed Mode

| | 1 Conventional | 2 Binderless | 3 Binderless | 4 Binderless | 5 Binderless |
|---|---|---|---|---|---|
| KF Water % | 5.4 | 3.88-4.17 | 3.88-4.17 | 4.42 | 4.42 |
| Cycle time, min | 34 | 34 | 23 | 34 | |
| $A/F_a$ | 0.68 | 0.51 | 0.51 | 0.51 | 0.51 |
| PX purity, % | 99.2 | 99.2 | 99.2 | 99.2 | 97.8 |
| PX recovery % | 95 | 95 | 95 | 93 | 96 |
| % PX over ADS-27 | — | 23% | | | |

The results in columns 1 and 2 of Table 2 show that a 23% improvement in para-xylene capacity was achieved using the binderless adsorbent comprising, barium-exchanged zeolite X, compared to the conventional, bound adsorbent. The results in column 3 show that the cycle time of the operation, using the binderless adsorbent, was reduced without adverse consequences. The results in column 4 show that increasing the water content of the binderless adsorbent did not appreciably improve the pilot plant operation.

The invention claimed is:

1. A process for separating para-xylene from a mixture comprising at least one other $C_8$ alkylaromatic hydrocarbon, the process comprising contacting, under adsorption conditions, the mixture with a binderless adsorbent comprising zeolite X and having a water content from about 3% to about 5.5% by weight to adsorb para-xylene, present in an adsorbed phase, in preference to the at least one other $C_8$ alkylaromatic hydrocarbon present in a non-adsorbed phase; flushing the non-adsorbed phase from contact with the adsorbent to produce a raffinate stream comprising the at least one other $C_8$ alkylaromatic hydrocarbon; and desorbing para-xylene in the adsorbed phase from the adsorbent to produce an extract stream comprising para-xylene; wherein the binderless adsorbent contains no amorphous material or the binderless adsorbent contains amorphous material in an amount less than about 2% by weight as determined by X-ray diffraction.

2. The process of claim 1, wherein the adsorbent has a water content from about 3.5% to about 4.5% by weight.

3. The process of claim 1, wherein the adsorption conditions include an adsorption temperature of less than about 175° C. (350° F.).

4. The process of claim 3, wherein the adsorption conditions include an adsorption temperature from about 130° C. (270° F.) to about 165° C. (330° F.).

5. The process of claim 1, wherein the binderless adsorbent comprises a converted portion of zeolite X resulting from the conversion of a zeolite X-precursor.

6. The process of claim 5, wherein the converted portion of zeolite X is present in an amount from about 5% to about 40% by weight, relative to the adsorbent.

7. The process of claim 5, wherein the converted portion of zeolite X has a silica to alumina molar ratio from about 2.3 to about 2.7.

8. The process of claim 1, wherein the zeolite X-precursor comprises kaolin clay.

9. The process of claim 1, wherein the adsorbent has at least 95% of its ion-exchangeable sites exchanged with barium or a combination of barium and potassium.

10. The process of claim 1, wherein the mixture comprises ortho-xylene, meta-xylene, para-xylene, and ethylbenzene.

11. The process of claim 10, wherein contacting the mixture with the adsorbent effects adsorption of para-xylene, present in the adsorbed phase, in preference to ortho-xylene, meta-xylene, and ethylbenzene, present in the non-adsorbed phase.

12. The process of claim 11, wherein para-xylene in the adsorbed phase is desorbed into the extract stream comprising a desorbent and the non-adsorbed phase is flushed into the raffinate stream comprising the desorbent.

13. The process of claim 12, wherein the desorbent comprises an aromatic ring-containing compound selected from the group consisting of toluene, benzene, indan, para-diethylbenzene, 1,4-diisopropylbenzene, and mixtures thereof.

14. The process of claim 13, wherein the process is performed in a simulated moving bed mode, wherein
    a feed stream and a desorbent stream are charged into a bed of the adsorbent, the feed stream comprising the mixture comprising ortho-xylene, meta-xylene, para-xylene, and ethylbenzene, and the desorbent stream comprising the desorbent; and wherein
    the extract stream and the raffinate stream are removed from the bed of the adsorbent.

15. The process of claim 14, wherein the process has a cycle time of less than about 34 minutes.

16. The process of claim 15, wherein the cycle time is from about 24 minutes to about 34 minutes.

17. The process of claim 16, wherein water is added to either or both of the feed stream and the desorbent stream to obtain a water content in the extract or raffinate stream from about 20 ppm by weight to about 120 ppm by weight.

18. The process of claim 15 wherein the adsorption conditions include an adsorption temperature from about 130° C. (270° F.) to about 165° C. (330° F.).

19. The process of claim 15 wherein the cycle time is from about 18 minutes to about 26 minutes.

* * * * *